US005585478A

United States Patent [19]
Lim et al.

[11] Patent Number: 5,585,478
[45] Date of Patent: Dec. 17, 1996

[54] D4 GENE AND METHODS OF USE THEREOF

[75] Inventors: Bing Lim, Dorchester, Mass.; Jean-Michel Lelias, Evry, France; Chaker N. Adra, Boston; Jone L. Ko, Sudbury both of Mass.

[73] Assignee: Beth Israel Hospital Association, Boston, Mass.

[21] Appl. No.: 292,945

[22] Filed: Aug. 18, 1994

Related U.S. Application Data

[63] Continuation of Ser. No. 990,337, Dec. 10, 1992, abandoned.
[51] Int. Cl.$^6$ .......................... C12N 15/11; C12N 15/12; C12Q 1/68
[52] U.S. Cl. .................. 536/23.5; 536/24.31; 536/24.33
[58] Field of Search ............................... 536/23.5, 24.31, 536/24.33

[56] References Cited

PUBLICATIONS

Greaves, M. F., et al. Lineage Promiscuity in Hemopoietic Differentiation and Leukemia. (1986) Blood 67:1–6.

Pui, C. H., et al. Characterization of Childhood Acute Leukemia with Multiple Myeloid and Lymphoid Markers at Diagnosis and at Relapse. (1991) Blood, 78:1327–1337.

McCulloch, E. A. Stem Cells in Normal and Leukemic Hemopoiesis (Henry Stratton Lecture, 1982). (1983) Blood 62:1–13.

Bradstock, K. F., et al. Unusual Immunophenotypes in Acute Leukaemias: Incidence and Clinical Correlations. (1989) Br. J. Haem. 75:512.

Klinken, S. P., et al. Hemopoietic Lineage Switch: v–raf Oncogene Converts Eµ–myc Transgenic B Cells into Macrophages, (1988) Cell 53:857–867.

Borzillo, G. V., et al, Macrophase Lineage Switching of Murine Early Pre–B–Lymphoid Cells Expressing Transduced fms Genes. (1990) Mol. Cell Biol. 10:2704–2174.

Fukumoto, Y., et al, Molecular Cloning and Characterization of a Novel Type of Regulatory Protein (GDI) for the rho Proteins, ras p21–like Small GTP–binding Proteins. (1990) Oncogene 5:1321–1328.

Sive, H., et al. A Simple Subtractive Hybridization Technique Employing Photoactivatable Biotin and Phenol Extraction. (1988) Nucleic Acid Research 16:10937.

Caput, D. et al. Identification of a Common Nucleotide Sequence in the 3'–untranslated Region of mRNA Molecules Specifying Inflammatory Mediators. (1986) PNAS 83:1670–1674.

Robertson, E. J. Embryo–derived Stem Cell Lines, (1987) Teratocarcinomas and embryonic stem cells, a practical approach, EJ Robertson (Ed.) 71–112. IRL Press.

Wiles, M. V., et al. Multiple Hematopoietic Lineages Develop from Embryonic Stem (ES) Cells in Culture, (1991) Development 111:259–267.

Sambrook, J., et al. Molecular Cloning, a Laboratory Manual, (1989) Cold Spring Harbor Laboratory Press.

Sanger, F., et al. (1977) Proc. Natl. Acad. Sci. 74:5463–5467.

Pinkle, D., et al. Fluorescence in situ Hybridization with Human Chromosome–specific Libraries: Detection of Trisomy 21 and Translocations of Chromosome 4. (1988) Proc. Natl. Acad. Sci. 85:9138–9142.

Weier, H. U., et al. Non–isotopical Labeling of Murine Heterochromatin In Situ by Hybridization with In Vitro–synthesized Biotinylated Gamma (Major) Satellite DNA. (1991) Bio Techniques.

Hart, M. J., et al. Catalysis of Guanine Nucleotide Exchange on the CDC42Hs Protein by the dbl Oncogene Product. (1991) Nature 354:211–314.

Satterthwaite, A. B., et al. Regulation of the Gene for CD34, a Human Hematopoietic Stem Cell Antigen, in KG–1 Cells. (1990) Blood 75:2299–2304.

Kurtzberg, J., et al. Establishment of the DU.528 Human Lymphohemopoietic Stem Cell Line. (1985) J. Exp. Med. 162:1561–1 578.

Scadden, D. T., et al. Human Immunodeficiency Virus Infection of Human Bone Marrow Stromal Fibroblasts. (1990) Blood 76:317–322.

Kyte, J., et al. (1982) J. Mol. Biol. 157:105–132.

Pearson, W. R., et al. Improved Tools for Biological Sequence Comparison. (1988) Proc. Natl. Acad. Sci. 85:2444–2448.

Schmitt, R. M., et al. Hematopoietic Development of Embryonic Stem Cells in vitro: Cytokine and Receptor Gene Expression, (1991) Genes & Development 5:728–740.

Whitelaw, E., et al. Regulated Expression of Globin Chains and the Erythroid Transcription Factor GATA–1 During Erythropoiesis in the Developing Mouse. (1990) Mol. Cell Biol. 10:6596–6606.

Miller, L. J., et al. Regulated Expression of the Mac–1, LFA–1, p 150, 95 Glycoprotein Family During Leukocyte Differentiation, (1986) J. Immunol. 137:2891–2895.

Stahl. P. D. (1990) *Am. J. Respir. Cell Mol. Biol.* 2:317–318.

(List continued on next page.)

*Primary Examiner*—Robert A. Wax
*Assistant Examiner*—Eric Grimes
*Attorney, Agent, or Firm*—Arnall Golden & Gregory

[57] ABSTRACT

The sequence, molecular structure and expression of a cDNA clone, denoted D4, of human and murine origin, preferentially expressed in hematopoietic cells is described herein. The human cDNA clone has been expressed in bacteria and the predicted 24 Kd protein purified. The protein has been used in studies of its biochemical function. As predicted on the basis of sequence, D4 can function as a GDP-dissociation inhibitor of at least several small GTP-binding proteins (CDC42 and rac). The D4 protein was used to generate a polyclonal antibody specific for the protein. The human cDNA was used to obtain several full length murine genomic clones. A clone has been analyzed and sequenced to use for the construction of a gene-targeting vector to produce animals deficient in D4 through disruption of the gene by homologous recombination. These animals can then be used as models for fundamental and applied research on the GTP-binding proteins.

8 Claims, 15 Drawing Sheets

PUBLICATIONS

Wong, P. M. C., et al. Properties of the Earliest Clonogenic Hemopoietic Precursors to Appear in the Developing Murine Yolk Sac. (1986) Proc. Natl. Acad. Sci.83:3851–3854.

Leonard, D., et al. The Identification and Characterization of a GDP–dissociation Inhibitor (GDI) for the CDC42Hs Protein. (1992) J. Biol. Chem. (in press).

Bradley, A., et al. Formation of Germ–line Chimaeras from Embryo–derived Teratocarcinoma Cell Lines, (1984) Nature 309:255–256.

Lindenbaum, M. H., et al. An in vitro Globin Gene Switching Model Based on Differentiated Embryonic Stem Cells, (1990) Genes & Development 4:2075–2085.

Simon, M. C., et al. Rescue of Erythroid Development in Gene Targeted GATA–1 Mouse Embryonic Stem Cells. (1992) Nature Genetics 1:92–98.

Carroll, A. J., et al. tdic(9;12): A Nonrandom Chromosome Abnormality in Childhood B–Cell Precursor Acute Lymphoblastic Leukemia: A Pediatric Oncology Group Study. (1987) Blood 70:1962–1965.

Raimondi, S. C., et al. New Recurring Chromosomal Translocations in Childhood Acute Lymphoblastic Leukemia. (1991) Blood 77:2016–2022.

Barbacid, M. ras Genes. (1987) Ann. Rev. Biochem. 56:779–827.

Kaziro, Y., et al. Structure and Function of Signal–transducing GTP–binding Proteins. (1991) Annual Review of Biochem 60:349–400.

Hall, A. Signal Transduction Through Small GTPases—A Tale of Two GAPS, (1992) Cell 69:389–391.

McCormick, F. ras GTPase Activating Protein: Signal Transmitter and Signal Terminator, (1989) Cell 56:5.

Hirai, H., et al. A Point Mutation at Codon 13 of the N–ras Oncogene in Myelodysplastic Syndrome. (1987) Nature 327:430–432.

Bos, J. L., et al. Amino–acid Substitutions at Codon 13 of the N–ras Oncogene in Human Acute Myeloid Leukaemia. (1985) Nature 315(27).726–730.

Madaule, P., et al. A Novel ras–related Gene Family. (1985) Cell 41:31–40.

Madaule, P., et al. Characterization of Two Members of the rho Gene Family from the Yeast *Saccharomyces cerevisiae*. (1987) Proc. Natl. Acad. Sci. USA 84:779–783.

Ellis, R. W., et al. (1981) The p21 src Genes of Harvey and Kirsten Sarcoma Viruses Originate from Divergent Members of a Family of Normal Vertebrate genes. (1987) Nature (London) 292:506–511.

Lowe, D. G., et al. Structure of the Human and Murine R–ras Genes, Novel Genes Closely Related to ras protooncogenes, (1987) Cell 48:137–146.

Chardin, P., et al, The ral Gene: A New ras–related Gene Isolated by the Use of a Synthetic Probe. (1986) Embo J. 5:2203–2208.

Pizon, V., et al. Human cDNAs rap 1 and rap 2 Homologous to the Drosophila Gene Dras3 Encode Proteins Closely Related to Ras in the effector Region. (1988) Oncogene 3:201–204.

Touchot, N., et al. Four Additional Members of the ras Gene Superfamily Isolated by Oligonucleotide Strategy: Molecular Cloning or YPT–related cDNAs from a Rat Brain Library. (1987) Proc. Natl. Acad. Sci. USA 84:8210–8214.

Vincent, S., et al. Growth–Regulated Expression of rhoG, a New Member of the ras Homolog Gene Family. (1992) Molecular and Cellular Biology 12(7):3138–3148.

Drivas, G. T., et al. Characterization of Four Movel ras–like Genes Expressed in a Human Teratocarcinoma Cell Line. (1990) Mol. Cell Biol. 10:1793–1798.

Avraham, H., et al. Characterization and Expression of the Human rhoH12 Gene Product. (1989) Mol. Cell Biol. 9:2058–2066.

Chardin, P., et al. The Mammalian G Protein rhoC is ADP–ribosylated by *Clostridium botulinum* Exoenzyme C3 and Affects Actin Microfilaments in Vero Cells. (1989) EMBO 8:1087–1092.

Ridley, A. J., et al. The Small GTP–binding Protein rho Regulates the Assembly of Focal Adhesions and Actin Stress Fibers in Response to Growth Factors. (1992) Cell 70:389–399.

Ridley, A. J., et al, The Small GTP–binding Protein rac Regulates Growth Factor–induced Membrane Ruffling. (1992) Cell 70:401–410.

Trahey, M., et al. Molecular Cloning of Two Types of GAP Complementary DNA from Human Placenta. (1988) Science 242:1697–1700.

Vogel, U. S., et al. Cloning of Bovine GAP and its Interaction with Oncogenic ras p21. (1988) Nature 335:90–93.

Tanaka, K., et al. *S. cerevisiae* Genes IRA1 and IRA2 Encode Proteins that may be Functionally Equivalent to Mammalian ras GTPase Activating Protein. (1990) Cell 60:803–807.

Imai, Y., et al. Identification of a GTPase–activating Protein Homolog in *Schizosaccharomyces pombe*, (1991) Mol. Cell Biol. 11, 3088–3094.

Garrett, M. D., et al. Identification of Distinct Cytoplasmic Targets for ras/R–ras and rho Regulatory Proteins. (1989) J. Biol Chem 264:10–13.

Katzav, S., et al. vav, a Novel Human Oncogene Derived from a Locus Ubiquitously Expressed in Hematopoietic Cells. (1989) EMBO Journal 8:2283–2290.

Toksoz, D., et al. Isolation and Cloning of Novel Oncogene LBC Detected by Transfection with Homology to Dbl. Cdc24 and Bcr. (in prep).

Matusui, Y., et al. Molecular Cloning and Characterization of a Novel Type of Regulatory Protein (GDI) for smg p25A, a ras p21–like GTP–binding Protein. (1990) Molecular and Cellular Biology 10:4116–4122.

Ueda, T., et al. Purification and Characterization from Bovine Brain Cytosol of a Novel Regulatory Protein Inhibiting the Dissociation of GDP from and the Subsequent Binding of GTP to rhoBp20, a ras p21–like GTP–binding Protein. (1990) J. Biol. Chem. 265:9373–9380.

Ellis, C., et al. Phosphorylation of GAP and GAP–associated Proteins by Transforming and Mitogenic Tyrosine Kinases. (1990) Nature 343:377–381.

Settleman, J., et al. Molecular Cloning of cDNAs Encoding the GAP–associated Protein p190: Implications for a Signaling Pathway from ras to the Nucleus. (1992) Cell 69:539–549.

Maru, Y., et al. The BCR Gene Encodes a Novel Serine/ Threonine Kinase Activity within a Single Exon. (1990) Cell 67:459–468.

Ron, D., et al. A Region of Proto–dbl Essential for its Transforming Activity Shows Sequence Similarity to a Yeast Cell Cycle Gene, CDC24, and the Human Breakpoint Cluster Gene, bcr (1991) New Biol. 3:372.

Diekmann, D., et al. Bcr Encodes a GTPase–activating Protein for $p21^{rac}$. (1991) Nature 351:400–402.

Shou, C., et al. Molecular Cloning of cDNAs Encoding a Guanine–nucleotide–releasing Factor for ras p21. (1992) Nature 358:351–354.

Koch, C. A., et al. SH2 and SH3 Domains: Elements that Control Interactions of Cytoplasmic Signaling Proteins. (1991) Science 252:668–674.

Hall, A. The cellular function of Small GTP–binding Proteins, (1990) Science 249:635–640.

Puil, L., et al. Vagaries of Vav. (1992) Cell Regulation 2:275–277.

Bollag, G., NF is Enough of a GAP, (1992) Nature 356:663–664.

Adams, J. M., et al. The Hematopoietically Expressed vav Proto–ocogene Shares Homology with the dbl GDP–GTP Exchange factor, the ber Gene and a Yeast Gene (CDC24) Involved in Cytoskeletal Organization. (1992) Oncogene 7:611–618.

Marx, J. New Genes May Shed Light on Cell Growth Control. (1992) Science 257:484–485.

Hershfield, M. S., et al. Treatment of Adenosine Deaminase Deficiency with Polyethylene Glycol–Modified Adenosine Deaminase, (1987) New Eng. J. Med. 316:589–596.

Tanaka, H., et al. Pharmacokinetics of Recombinant Human Granulocyte Colony–stimulating Factor Conjugated to Polyethylene Glycol in Rats. (1991) Cancer Research 51:3710–3714.

Kitamura, K., et al. Chemical Engineering of the Monoclonal Antibody A7 by Polyethylene Glycol for Targeting Cancer Chemotherapy. (1991) Cancer Research 51:4310–4315.

Hershfield, M. S., et al. Use of Site–directed Mutagenesis to Enhance the Epitope–shielding Effect of Covalent Modification of Proteins with Polyethylene Glycol. (1991) Proc. Natl. Acad. Sci. USA 88:7185–7189.

Gregoriadis, G. ed. Liposomes as Drug Carriers (Wiley, New York), pp. 1–863 (1988).

Papahadjopoulos, D., et al. Sterically Stabilized Liposomes: Improvements in Pharmacokinetics and Antitumor Therapeutic Efficacy. (1991) Proc. Natl. Acad. Sci. USA 88:11460–11464.

Maruyama, K., et al. Lipid Composition is Important for Highly Efficient Target Binding and Retention of Immunoliposomes, (1990) Proc. Natl. Acad. Sci. USA 87:5744–5748.

Hughes, B. J., et al. Monoclonal Antibody Targeting of Liposomes to Mouse Lung in Vivo, (1989) Cancer Research 49:6214–6220.

Lopez–Berestein, G., et al. Liposomal Amphotericin B for the Treatment of Systemic Fungal Infections in Patients with Cancer: A Preliminary Study. (1985) J. Inf. Dis. 151:704–710.

Vitetta, E. S., et al. Redesigning Nature's Poisons to Create Anti–tumor Reagents, (1987) Science 238:1098–1104.

Pastan, I. P., et al. Immunotoxins, (1986) Cell 47:641–648.

Leamon, C. P., et al. Delivery of Macromolecules into Living Cells: A Method that Exploits folate Receptor Endocytosis, (1991) Proc. Natl. Acad. Sci. USA 88:5572–5576.

Wagner, J. A., et al. Antisense Oligodeoxynucleotides to the Cystic Fibrosis Transmembrane Conductance Regulator Inhibit cAMP–activated but not Calcium–activated Chloride Currents. (1992) Proc. Natl. Acad. Sci. 89:6785–6789.

Prochownik, E. V., et al. Antisense Transcripts Accelerate Differentiation and Inhibit $G_1$ Progression in Murine Erythroleukemia Cells. (198) Mol. Cell Biol. 8:3683–3695.

Wickstrom, E. L., et al. Human Promyelocytic Leukemia HL–60 Cell Proliferation and c–myc Protein Expression are Inhibited by an Antisense Pentadecadeoxynucleotide Targeted Against c–myc mRNA. (1988) Proc. Natl. Acad. Sci. 85:1028–1032.

Wang, H., et al. Antisense Oligodeoxynucleotides to G. Protein $\alpha$–subunit Sequence Accelerate Differentiation of Fibroblasts to Adipocytes. (1992) Nature 358:334–337.

Skorski, T., et al. Growth Factor–dependant Inhibition of Normal Hematopoiesis by N–ras Antisense Oligodeoxynucleotides. (1992) J. Exp. Med. 175:743–750.

Bayever, E., et al. Leukemias/Myelodysplasia and Myeloproliferative Disorders–III. (1992) Blood 80, Suppl 1, Abstract 833.

Miller, A. D. Human Gene Therapy Comes of Age. (1992) Nature 357:455–460.

Rosenfeld, M. A., et al. In Vivo Transfer of the Human Cystic Fibrosis Transmembrane Conductance Regulator Gene to the Airway Epithelim. (1992) Cell 68:143–155.

van Beusechem. V. W., et al. Long–term Expression of Human Adenosine Deaminase in Rhesus Monkeys Transplanted with Retrovirus–infected Bone–marrow Cells. (1992) Proc. Natl. Acad. Sci. 89:7640–7644.

Lemarchand, P., et al. Adenovirus–mediated Transfer of a Recombinant Human $\alpha_1$–antitrypsin cDNA to Human Endothelial Cells, (1992) Proc. Natl. Acad. Sci. 89:6482–6486.

Zenke, M., et al. Receptor–mediated Endocytosis of Transferrin–polycation Conjugates: An efficient Way to Introduce DNA Into Hematopoietic Cells. (1990) Proc. Natl. Acad. Sci. USA, 87:3655–3659.

Curiel, D. T., et al. Adenovirus Enhancement of Transferrin–polylysine–mediated Gene Delivery, (1991) Proc. Natl. Acad. Sci. 88:8850–8854.

Wu, G. Y., et al. Receptor–mediated Gene Delivery in Vivo. (1991) J. Biol. Chem. 266:14338–14342.

Wong, G., et al. Molecular Cloning and Nucleic Acid Binding Properties of the GAP–associated Tyrosine Phosphoprotein p62, (1992) Cell 69:551–558.

Blanar, M. A., et al. Interaction Cloning: Identification of a Helix–Loop–Heliz Zipper Protein that Interacts with c–Fos. (1991) Science 256:1014–1018.

LeClair, K. P., et al. The p50 Subunit of NF–kB Associates with the Nf–IL6 Transcription Factor. (1992) Proc. Natl. Acad. Sci. USA, 89:8145–8149.

Cicchetti, P., et al. Identification of a Protein that Binds to the SH3 Region of Abl and is Similar to Bcr and GAP–rho. (1992) Science 257:803–806.

Kaelin, W. G., et al. Expression Cloning of a cNDA Encoding a Retinoblastoma–binding Protein with E2F–like Properties, (1992) Cell 70:351–364.

Capecchi, M. R. Altering the Genome by Homologous Recombination. (1989) Science 244:1288–1292.

Koller, B. H. Altering Genes in Animals by Gene Targeting. (1992) Ann. Rev. Immunol. 10:705–730.

Travis, J. Scoring a Technical Knockout in Mice. (1992) Science 256:1392–1394.

Adra et al., J. Cell Biochem. 16c (Suppl.):93 (1992).

Adra et al., Genes Chrom. Cancer 8:253–261 (1993).

Lelias et al., Proc. Natl. Acad. Sci. USA 90:1479–1483 (1993).

Fukumoto, Y. et al., Oncogene 5:1321–1328 (1990).

```
m D4      MTEKDAQPQLEEA...DDD.LDSKLNYKPPPQKSLKFLQEMDKDDESLTK    46
h D4      MTEKAPEPHVEED...DDDELDSKLNYKPPPQKSLKELQEMDKDDESLIK    47
b rhoGDI  MAEQEPTAEQLAQIAAENEEDEHSVNYKPPAQKSIQEIQELDKDDESLRK    50 m D4      YKKTLLGDVPVVADPTVPNVTVTRLSLVCDSAPGPITMDLTGDLEALKKD    96
h D4      YKKTLLGDGPVVTDPKAPNVVVTRLTLVCESAPGPITMDLTGDLEALKKE    97
b rhoGDI  YKEALLGRVAVSADPNVPNVVTRLTLVCSTAPGPLELDLTGDLESFKKQ    100
                              G  S m D4      TFVLKEGIEYRVKINFKVNKDIVSGLKYVQHTYRTGMRVDKATFMVGSYG   146
h D4      TIVLKEGSEYRVKIHFKVNRDIVSGLKYVQHTYRTGVKVDKATFMVGSYG   147
b rhoGDI  SFVLKEGVEYRIKISFRVNREIVSGMKYIQHTYRKGVKIDKTDYMVGSYG   150
h rhoGDI                                                V
```

```
m D4      PRPEEYEFLTPYFEAPKGMLARGTYHNKSFFTDDDKQDHLTWEWNLAIKK  196
          |||*|||||||||*|||||||||||||||||||||||||||*|||
h D4      PRPEEYEFLTPVEEAPKGMLAQDTYHNKSFFTDDDKQDHLSWEWNLSIKK  197
          ||*|||||||||*|||||||||||*|  |||||||||*|||||||*|||
b rhoGDI  PRAEEYEFLTPMEEAPKGMLARGSYNIKSRFTDDDRTDHLSWEWNLTIKK  200 h rhoGDI         *            V          ..      *      K
                                          S m D4      DWTE  200
          |||*
h D4      EWTE  201
          ||*|
b rhoGDI  EWKD  204 h rhoGDI   *
           D
```

D4 GENE AND METHODS OF USE THEREOF

The United States government has rights in this invention by Virtue of support by a National Institute of Health grant No. DK 44099-02.

This is a continuation of application Ser. No. 07/990,337 filed on Dec. 10, 1992, now abandoned.

BACKGROUND OF THE INVENTION

The present invention is generally in the area of regulation of proliferation and differentiation of hematopoietic cells, and is more specifically the nucleic acid sequence encoding a protein called D4, and methods of use thereof in regulation of hematopoietic cells.

In the hematopoietic system, a common pluripotent stem cell gives rise to at least eight distinct lineages. While cells of each lineage appear to have strictly defined characteristics and function, a considerable plasticity in lineage specificity at the cellular and molecular level had been observed. For example, leukemic cells had been found to express molecular markers of more than one lineage in the same cell, as reported by Pui C. H., Raimondi S. C., Head D. R., Schell M. J., Rivera G. K., Mirro J. Jr., Crist W. M., Behm F. G. (1991) Blood 78:1327–1337; McCulloch E. A. (1983) Blood 62:1–13; Bradstock K. F., Kirk J., Grimsley P. G., Kabral A, Hughes W. G. (1989) Br J Haem 75:512; and Greaves M. F., Chan L. C., Furley A. J. W., Watt S. M., Mulgaard N. Y. (1986) Blood 67:1–6. It is unclear at the moment whether this reflects a distortion of the genetic mechanism of differentiation (McCulloch) or the normal differentiation process of stem cells (Greaves, et al.). A more dramatic example of this plasticity is the demonstration of the conversion of pre-B cells, which had undergone VDJ rearrangement, into macrophages Klinken S. P., Alexander W. S., Adams J. H. (1988) Cell 53:857–867; and Borzillo G. V., Ashmun R. A., Sherr C. J. (1990) Mol. Cell Biol. 10:2704–2174. These "de-differentiated" cells continue to maintain their immunoglobulin gene rearrangements but morphologically and functionally behave as macrophages.

It is remarkable that cells with a stably rearranged genome can convert into cells of a completely different lineage. These observations suggest that beneath the diversity some or all hematopoietic lineages continue to remain closely related. Hematopoietic cells may then be viewed not as a system of distinctly differentiated cells but as a family of related cells amongst which common features may be detected which distinguish them from other tissues.

It is surmised that there are molecules which regulate molecular events unique to all hematopoietic cells and that these molecules are likely to be important even after commitment into specific lineages.

It is therefore an object of the present invention to provide a gene, and the protein encoded thereby, which is involved in the proliferation and differentiation of hematopoietic cells.

It is a further object of the present invention to provide methods of use for the protein, and inhibition or expression of the gene for the protein, to enhance or limit hematopoietic cell proliferation and differentiation.

SUMMARY OF THE INVENTION

By the differential screening of a subtractive hematopoietic-cell cDNA library with subtractive probes, the cDNA clones of several genes not previously identified which are preferentially expressed in hematopoietic cells have been identified and isolated. The sequence, molecular structure and expression of one of these clones, denoted D4, of human and murine origin, is described herein. Transcripts for D4 are expressed preferentially at a very high level in hematopoietic cells of all lineages. Transcripts are also detected at a lower level in non-hematopoietic cell lines and tissues, including melanoma cells, neuroblastoma cells, skeletal muscles, lung and fat cells. D4 protein expressed from the cDNA in bacteria demonstrated GDP-dissociation inhibitor (GDI)-like activity. D4 is therefore believed to be useful in regulation of proliferation and differentiation of hematopoietic cells.

Using the cDNA, the human D4 gene has been localized to chromosome 12p 12–13, an area involved in chromosomal translocations and deletions of 10% of childhood acute lymphoid leukemia. The cDNA can be used diagnostically in examining DNAs from leukemic patients for identification of sub-types of leukemia. Confirmation of the involvement of D4 in these leukemias will be of great clinical and therapeutic significance. D4 protein will be used as a labelled probe to search for and isolate interacting protein(s).

The human cDNA clone has been expressed in bacteria and the predicted 24 Kd protein purified. The protein has been used in studies of its biochemical function. As predicted on the basis of sequence, D4 can function as a GDP-dissociation inhibitor of at least several small GTP-binding proteins (CDC42 and rac).

The D4 protein was used to generate a polyclonal antibody specific for the protein. The antibody can be used to identify other putative small GTP-binding proteins which interact with D4. The antibody will also be useful in diagnostic and research applications.

The human cDNA was used to obtain several full length murine genomic clones. A clone has been analyzed and sequenced to use for the construction of a gene-targeting vector to produce animals deficient in D4 through disruption of the gene by homologous recombination. These animals can then be used as models for fundamental and applied research on the GTP-binding proteins. It is believed that D4 activity is required for progression of differentiation and growth; a reduced or absence of D4 activity would arrest terminal differentiation. This thesis is supported by the following observations: a) a dramatic increase in D4 transcripts during proliferation and differentiation of the earliest hematopoietic precursors isolated from day 9 murine yolk sac cells and b) different changes in the level of D4 transcripts during induced differentiation of various hematopoietic cell lines.

Therefore, potential clinical use of D4 involves the manipulation of cell growth and differentiation in normal cells and in treatment of some leukemias. For example, to induce differentiation of leukemic cells defective in the gene, D4 would be administered to cells using protein carriers to effectively deliver the protein into cells. To transiently arrest differentiation such as during efforts to amplify hematopoietic stem cells in vitro before bone-marrow transplantation, the production of D4 protein would be inhibited using anti-sense oligonucleotides or ribozyme technology.

BRIEF DESCRIPTION OF THE DRAWINGS

FIG. 2A is 15 μg of total RNA resolved on a denaturating agarose gel, transferred to Hybond-N™ filters (Amersham), hybridized with $^{32}$P-labelled D4 cDNA probe and washed with 0.2×SSC at 65° C. before autoradiography for 24 hrs at −80° C. FIG. 2B is the gel of FIG. 2A stained with Ethidium bromide to monitor integrity of samples and constancy of loading. Tissues are hemapoietic cells: K562, OCIR, KG-1, LY17, OCI-MYI, DU528, and bone marrow; and non-hematopoietic cells: BS-1, HEPG2, CALU-1, SKMEL, HS294, HELA, HUSK, and SKNSH cells.

FIG. 3A is an autoradiograph of the gel. FIG. 3B is the gel of FIG. 3A stained with Ethidium Bromide. Tissues are bone marrow, T-lymphocyte, skin fibroblast, brain, kidney, lung, liver, adrenal and skeletal muscle.

FIG. 4A is the hybridized membrane was washed at 0.2×SSC, 65° C. for 1 hr and autoradiographed for 24 hrs at −80° C. Lower stringency hybridizing and washing condition did not reveal additional or stronger signals. FIG. 4B is gel stained with Ethidium Bromide.

FIG. 5 is a comparison of murine (m) and human (h) D4 with bovine (b) and human (h) rhoGDI protein sequences using the FASTA program of Pearson and Lipman, (1988) Proc. Natl. Acad. Sci. 85:2444–2448. Vertical lines indicate identical matches and asterisks indicate conservative changes. Gaps introduced to maximize alignment are indicted by dots.

FIG. 7A is U937 induced with TPA. The same blot was probed sequentially, (A) with D4 and (S) with CD11b. FIG. 7B is HL60 induced with DMSO. FIG. 7C is MEL induced with DMSO.

FIG. 9A is the purification of malE-D4 from E. coli. The proteins were stained with Coomassie brilliant blue. Lanes: 1, protein molecular weight marker; 2, bacterial homogenate before IPTG induction; 3, bacterial homogenate after IPTG induction; 4, bacterial pellet after sonication; 6, eluted pools from amylose column; 7, eluted pools from Q-Sepharose™ column; 8, molecular weight markers. FIG. 9B is the cleavage of D4 from malE-D4 with factor Xa and further purification for iD4. 10 μg factor X was added to maltose free mal-D4 protein solution and digestion completed after 12 hours incubation at room temperature. Male was separated from D4 by passing through amylose column. Male binds to amylose and D4, approximately 90% pure, was collected in flow through fractions. Lanes 1 and 2 eluted pools from Q-Sepharose™ column; lane 3, pure D4.

FIG. 10A is the principle of the GDI assay. FIG. 10B is the dose response of the rhoGDI GDI activity on CDC42. The S. frugiperda-expressed CDC42Hs was pre-incubated with 7 μM [α-$^{32}$P]GTP for 25 min at room temperature. This incubation converts all of the bound GTP to GDP. The [α-$^{32}$P]GTP-labeled CDC42Hs proteins (approximately 15 ng) were then incubated with the indicated amounts of Mono-S-purified CDC42Hs-GDI activity in the presence of 2.5 mM EDTA and no added MgCl$_2$. After 6 minutes, the samples were filtered on nitrocellulose (BA85) filters and the amount of the [α-$^{32}$P]GTP which remained bound to the CDC42Hs protein relative to the amount of radiolabelled guanine nucleotide that was bound at the start of the assay, as a function of the amount of GDI added to the assay incubation, was determined. FIG. 10C is the dose response of D4-GDI activity on CDC42Hs. FIG. 10D is the dose response of D4 -GDI activity on rac 1.

DETAILED DESCRIPTION OF THE INVENTION

Figure 1:
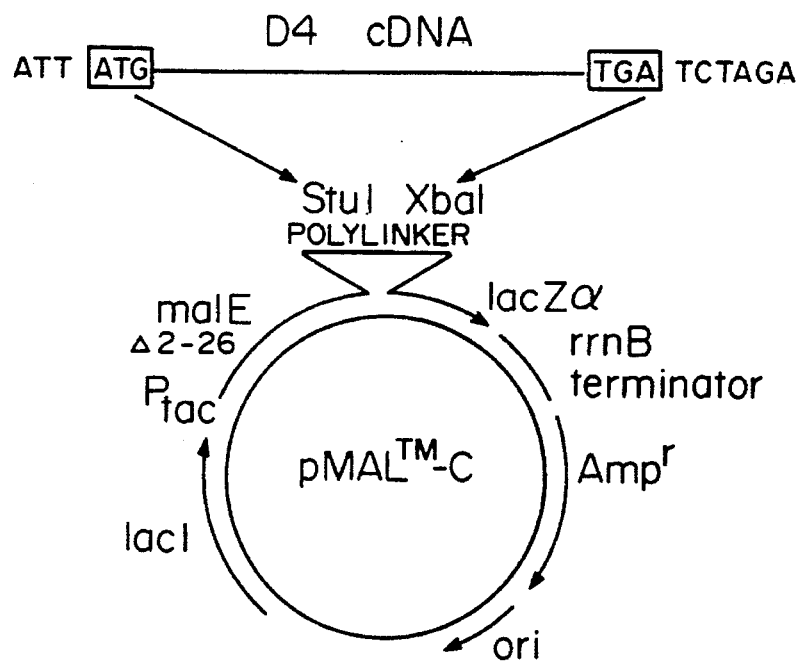
FIG. 1 is a diagram of the vector and scheme used to generate the D4 (D4)-fusion protein.

A gene which has not previously been reported was isolated from a clone predominantly expressed in hematopoietic cells. The D4 cDNA encodes a protein with homology to bovine rhoGDI, recently described by Fukomoto, et al., (1990), a GDP-dissociation inhibitor (GDI) for the rho(ras-homologous) proteins (although homologous, the sequence and structural homology is insufficient to use probes from the rhoGDI to obtain the D4 gene).

Human and murine D4 cDNA and the gene were isolated as described below. The equivalent gene could be isolated from other mammalian species using the same methodology.

MATERIALS AND METHODS

Cell Lines.

Hematopoietic cell-lines included pluripotential (DU528, K562 ), erythro-leukemia (HEL, OCIR), monoblastic (U937), myeloblastic (KG-1), promyelocytic (HL60), T-cell lymphoma and leukemia (LY-17, Molt-4), myeloma (OCIMy1), megakaryocytic (Dami) and murine erythroleukemia (MEL) cells. Non-hematopoietic cell-lines were bone marrow stromal (BS-1), hepatoma (HepG2), lung cancer (Calu-1), cervical cancer (HeLa), melanoma (HS294, SKMEL), skeletal muscle (HuSk), neuroblastoma (SKNSH), and skin fibroblasts. All cell lines were maintained in Iscove's modified Dulbecco's medium (IMDM) supplemented with 10% fetal bovine serum (FBS) and 1 mM L-glutamine, except for DU528 where horse serum replaced FBS. All cell lines were obtained from the American Type Culture Collection (ATCC) except where acknowledged.

Construction of subtractive CDNA libraries.

Three hematopoietic cell lines (K562, KG-1 and DU528) and a non hematopoietic human bone-marrow stromal line (BS-1) were used in the construction of subtractive CDNA libraries and generation of probes for differential screening. cDNAs made from the four cell lines were hybridized with an excess of BS-1 MRNA. Unhybridized cDNAS were separated by a cDNA-mRNA hybridization technique as described by Sive et al (1988) Nucleic Acid Research 16:10937. mRNAs of BS-1 were biotinylated with photobiotin acetate (Invitrogen) following protocol recommended by vendor. cDNA-biotinylated mRNA hybrids and excess biotinylated mRNAS were removed by treatment with strepavidin (Invitrogen) followed by phenol extraction leaving unhybridized cDNAs in the aqueous phase. Two rounds of subtractive hybridization were performed. The resulting unhybridized cDNAs were used to construct four libraries (K562/BS-1, KG-1/BS-1, DU528/BS-1 and BS-1/BS-1) as described by Caput et al (1986) PNAS 83:1670–1674, using the PT3T719U multi-phagemid vector (Pharmacia). cDNAs were cloned directionally into the Pst 1 and BamH1 sites.

Generation of DNA probes from subtractive libraries.

Recombinant DNA was purified from the KG-1/BS-1, DU528/BS-1 and BS-1/BS-1 subtractive libraries. cDNA inserts were released by restriction enzymes Pst1 and BamH1, purified on low-melt agarose electrophoretic gel and labelled with $^{32}P$ using multi-prime labelling (Pharmacia).

Cloning of murine D4.

A phage CDNA library in lambdaASHlox vector (Novagen, Madison, Wis.) derived from 15 day embryo RNAs was screened with the human D4 cDNA following the technique described by (Sambrook et al (1989) Molecular Cloning, a Laboratory Manual. Cold Spring Harbor Laboratory Press). Hybridization and washing was carried out under high stringency conditions. Positive clones were identified by radiography and individual clones isolated by two rounds of secondary screening. DNA from selected clones were extracted as described. cDNA was analyzed by Southern analysis after restriction digestion.

In vitro differentiation of murine Embryonal Stem (ES) cells.

The CCE ES line was maintained and passaged as described by Robertson E. J. (1987) Teratocarcinomas and embryonic stem cells, a practical approach. E. J. Robertson, Ed. 71–112 (IRL Press) in the presence of Leukemic Inhibitory Factor (LIF, Genetics Institute, Cambridge). Differentiation of totipotent ES cells into hematopoietic cells was studied with an in vitro assay similar to that described by Wiles et al., (1991) Development 111:259–267. Single cell suspension of the CCE cell line were cultured in non-tissue culture 35 mm dishes (Fisher) with a mixture containing 0.9% methyl-cellulose (Fluka), 20% FBS (Hyclone), 1% bovine serum albumin, 2 u/ml erythropoietin (Dr. D. Worchowski, Pennsylvania State University), 50 ng/ml Stem cell factor (Amgen) and 200–400 u/ml IL-1 (Hoffman LaRoche) at a cell concentration of 1000–2000 cells per ml. Incubation was carried out in a humidified atmosphere at 37° C. and colonies examined and collected at different days after initiation of culture by pooling colonies from several dishes.

Induction of cell lines.

The cell lines U937, HL60 and MEL were grown to a concentration of $5\times10^6$ cells/ml before initiation of induction: U937 was induced with $5\times10^{-8}M$ 12-0-tetradecanoyl-phorbol-13-acetate (TPA, Sigma); HL60 was induced with TPA or 4% dimethyl sulfoxide (DMSO); MEL was induced with 1.5% DMSO.

General Methods.

Standard methods were carried out as described in Sambrook et al (1989) Molecular Cloning, a Laboratory Manual. Cold Spring Harbor Laboratory Press, the teachings of which are specifically incorporated herein. RNA was isolated using the guanidinium isothiocyanate/CsCl procedure. DNA sequencing was done by the dideoxynucleotide chain-termination technique of Sanger F., Milken S., Coulson A. R. (1977) Proc. Natl. Acad. Sci. 74:5463–5467 after subcloning appropriate DNA fragments into M1 3.

Chromosomal mapping.

D4 gene was localized by the fluorescent in-situ hybridization (FISH) technique of Pinkle, et al. (1988) Proc. Natl. Acad. Sci. 85:9138–9142. Metaphase chromosomes were obtained from phytohemaglutinin (PHA) stimulated peripheral blood cells. Fluorescence-conjugated human D4 CDNA was hybridized to chromosomal spreads and processed as described by Weier H. U., Zitzelsberger, Gray J. W. (1991) Bio Techniques 10(4), 498–505. More than twenty metaphases were examined and analyzed under UV-light activated microscopy.

Generation of fusion proteins of D4.

Construction of expression vector

A D4 expression vector was constructed using the pMAL vector (New England BioLab). A gene segment containing the entire coding region for human D4 protein was generated by the polymerase chain reaction (PCR) technique, using a pair of primers, D4-N2 and D4-C2. D4-N2 (5'-ATT ATG ACT GAA AAA GCCCCA GAG CCACATGTG-3') (Sequence ID No. 1) is a 33 met spanning from nucleotides 75 to 104 of the D4 sequence and including three additional nucleotides, ATT, located immediately 5' of the ATG site of the D4 gene. D4-C2(5'-GACTCTAGATCATTCTGTC-CACTCCTTCTT-3') (Sequence ID No. 2) is a 30 mer spanning from nucleotides 660 to 680 and containing a newly added XbaI restriction site 3' to the TGA (nucleotides 678–680). The resulting D4 fragment has a length of 618 base pairs.

The D4 DNA segment was digested with the XbaI enzyme and subcloned into the PMAL-C vector (New England BioLab, Beverly, Mass.) which was digested at the StuI and XbaI sites, as shown in FIG. 1. The resulting D4 expression vector, pMAL-D4, was used for the expression of fusion protein, Mal-D4, with a maltose binding domain at its N-terminal half and a complete D4 protein at its C terminal half.

Expression and isolation of D4 protein.

The pMAL-D4 vector was transformed into DH5α bacterial host for the expression of Mal-D4 fusion. Ten ml of an overnight culture of recipient DH5α cells were seeded into one liter of LB broth containing 100 μg/ml of ampicillin. The seeded bacterial culture was incubated at 37° C. under continuous shaking conditions until it reached 0.45 $OD_{650}$. The induction of the production of the Mal-D4 fusion protein was initiated by the addition of IPTG to a final concentration of 0.3 mM. The culture was allowed to continue for another four hours.

The induced culture was pelleted and resuspended in 50 mL of lysis buffer (20 mM Tris-HCl, pH 7.4, 200 mM NaCl, 1 mM EDTA and 1 mM sodium azide) containing 1 mg/mL of lysozyme. This cell suspension was subjected to one cycle of freeze-thaw and then sonicated to complete lysis. The lysate was spun at 10,000 g, 40° C. for 30 min, and the soluble lysate was collected, diluted five fold with lysis buffer and passed through a 20 mL amylose column (New England Biolab, Beverly, Mass.). The column was subsequently washed with 100 mL of lysis buffer and eluted with lysis buffer containing 10 mM maltose. Fractions containing mal-D4 protein were pooled, diluted four fold with 20 mM Tris-HCl pH 8.0, passed through 1 mL of Q-sepharose™ column (Pharmacia, N.J.). The Q-sepharose™ column was then washed with 20 mL of 20 mM Tris-HCl, pH 8.0 with 50 mM NaCl and eluted with buffer containing 20 mM Tris HCl, pH 8.0 and 0.75M NaCl. The Q-sepharose column™ was used to remove the free maltose from the mal-D4 fusion protein, prior to cleaving the fusion protein with factor Xa (New England Biolab, Beverly, Mass.). 10 μg of factor Xa was added to the mal-D4 fusion protein; the digestion was completed after a 12 h incubation at room temperature. To separate D4 protein from the maltose binding domain (mal), the digestion mixture was diluted two fold with lysis buffer and passed through a 20 mL amylose column. While the mal protein bound to the amylose column, the D4 protein was present in the flow-through fractions. In general, the purity of the D4 protein was around 90%. This D4 protein, iD4, is preceded by an extra isoleucine as a result of factor Xa cleavage.

Biochemical Function studies.

The ability of the iD4 or D4 protein to inhibit the dissociation of GDP from CDC42Hs was measured by nitrocellulose filter binding assay. Specifically, 15 ng of CDC42Hs purified from human platelets as described by Hart et al. (1991) Nature 354:311–314 was incubated with 0.625 μM GTP-α-$^{32}$P in 20 mM Tris-HCl pH 8.0, 0.725 mM dithiothreitol, 10 mM $MgCl_2$, 50 mM NaCl, 100 μM AMP-PNP for a period of 25 minutes. Previous experiments have shown that the GTP binds to CDC42Hs and is completely hydrolyzed to GDP during this incubation. Aliquots of this binding mixture (¹⁄₁₆ of the total) were then diluted 10-fold into a tube containing the indicated amounts of the iD4 fusion protein and a final concentration of 34 mM Tris-HCl pH 8.0, 160 μM dithiothreitol, 205 mM NaCl, 1 mM $MgCl_2$, 3.3 mM EDTA, 200 μM GDP, 220 μM μMP-PNP, and 100 μg/ml bovine serum albumin. After a six minute incubation to allow dissociation, 0.5 ml of cold dilution buffer (20 mM Tris-HCl pH 8.0, 100 mM NaCl, 10 mM $MgCl_2$) was added to the mixture and subsequently filtered on nitrocellulose (BA-85, Schleicher and Schuell). The filters were washed 3 times with dilution buffer to remove free nucleotide, and the radioactivity associated with the filter was determined by liquid scintillation counting.

RESULTS

Construction of subtractive libraries.

cDNA libraries of hematopoietic cell lines that are enriched for cDNAs of mRNA preferentially or uniquely expressed in hematopoietic cells were constructed. This was achieved by subtracting cDNAs of the hematopoietic cell-lines with mRNAs from a non-hematopoietic cell-line. The hematopoietic cell lines were chosen on the basis of their primitive stem cell characteristics. K562 cells express markers for erythroid, granulocytic and megakaryocytic lineages, as reported by McCulloch E. A. (1983) Blood 62:1–13. KG-1 cells, a myeloblastic line, express the CD34 surface antigen, as reported by Satterthwaite A. B., et al., (1990) Blood 75:2299–2304, a marker for multipotential stem cells. DU528 cells, derived from a patient with leukemia, have been shown by Kurtzberg, et al. (1985) J. Exp. Med. 162:1561–1578, to be capable of differentiating into both lymphoid and myeloid lineages. Since the objective of subtraction was to reduce the complexity of the libraries, the choice of the non-hematopoietic mRNAs used for subtraction was made arbitrarily, a human bone-marrow stromal derived line, BS-1, described by Scadden, et al. (1990) Blood 76:317–322. Two rounds of subtraction were performed before the cDNAS were used to construct the libraries. A "normalized" stromal BS-1 cDNA library enriched for low frequency molecular species was also constructed using the stromal cDNAs obtained after subtracting twice with stromal mRNAs.

Differential screening and identification of hematopoietic specific clones.

The established libraries became a ready source of probes. cDNA inserts from two hematopoietic (DU528 and KG-1) and the BS-1 subtractive libraries were released and purified. The three probes were then used to hybridize against triplicates of the K562 library. Colonies hybridizing with the hematopoietic-probes (DU528 and KG-1) and not with the BS-1 probe were isolated and expanded. DNAs from these clones were extracted and used as individual probes to examine Northern blots consisting of a panel of total RNAs from hematopoietic and non-hematopoietic cell lines. The patterns of expression allowed us to identify CDNA clones of different mRNAs which are either preferentially or specifically expressed in hematopoietic cells.

Identification of clone D4.

Figures 2A, 2B:
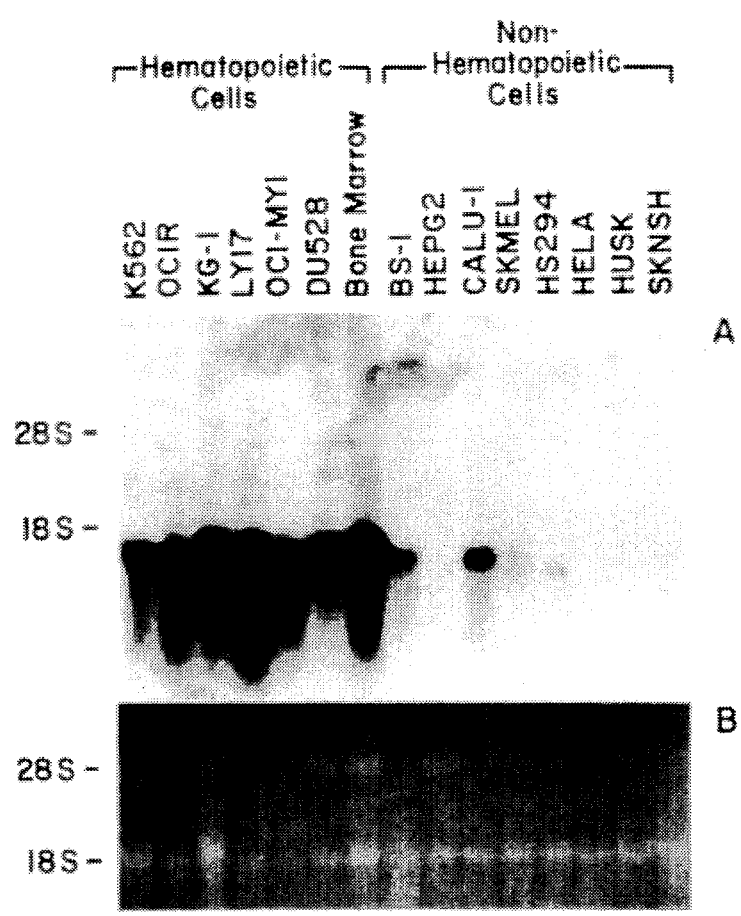
FIGS. 2A and 2B are a Northern analysis of D4 mRNA in human hematopoietic and non-hematopoietic cell lines.

Clone D4 contains an insert which detects a 1.5 kb D4 transcript present in great abundance in hematopoietic cell lines of myeloid and lymphoid, as shown by FIG. 2. In contrast non-hematopoietic cell lines either do not express the transcript (HepG2, HeLa) or do so at a much lower level. Only cell lines of bone-marrow stroma (BS-1) and lung (Calu-1) expressed a comparable level of D4 but even in these cells, the levels of D4 expressed were consistently lower than in hematopoietic cells.

Expression of D4 in normal human and murine tissues.

Figures 3A, 3B:
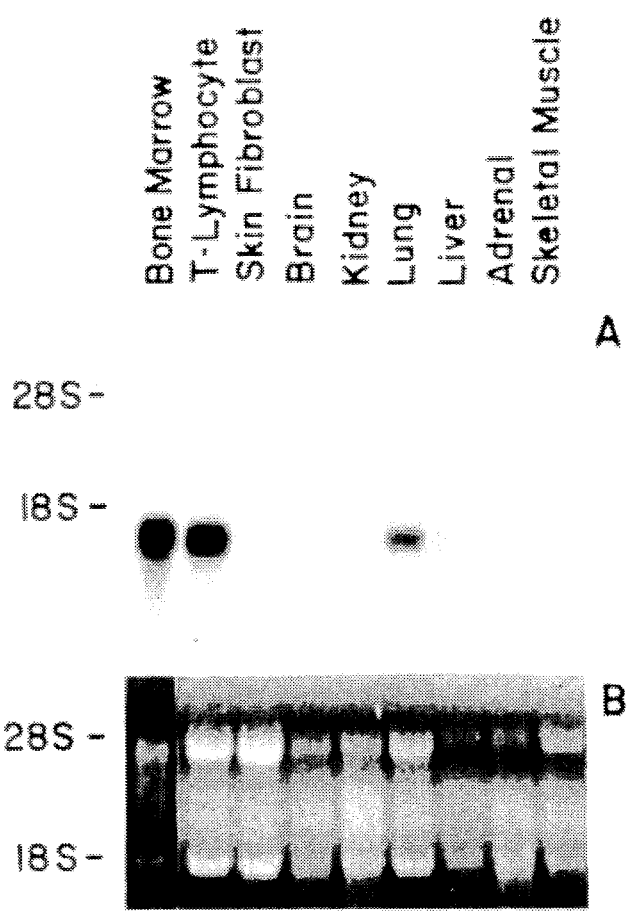
FIGS. 3A and 3B are a Northern analysis of D4 in 15 μg RNA samples extracted from normal human tissues.
Figures 4A, 4B:
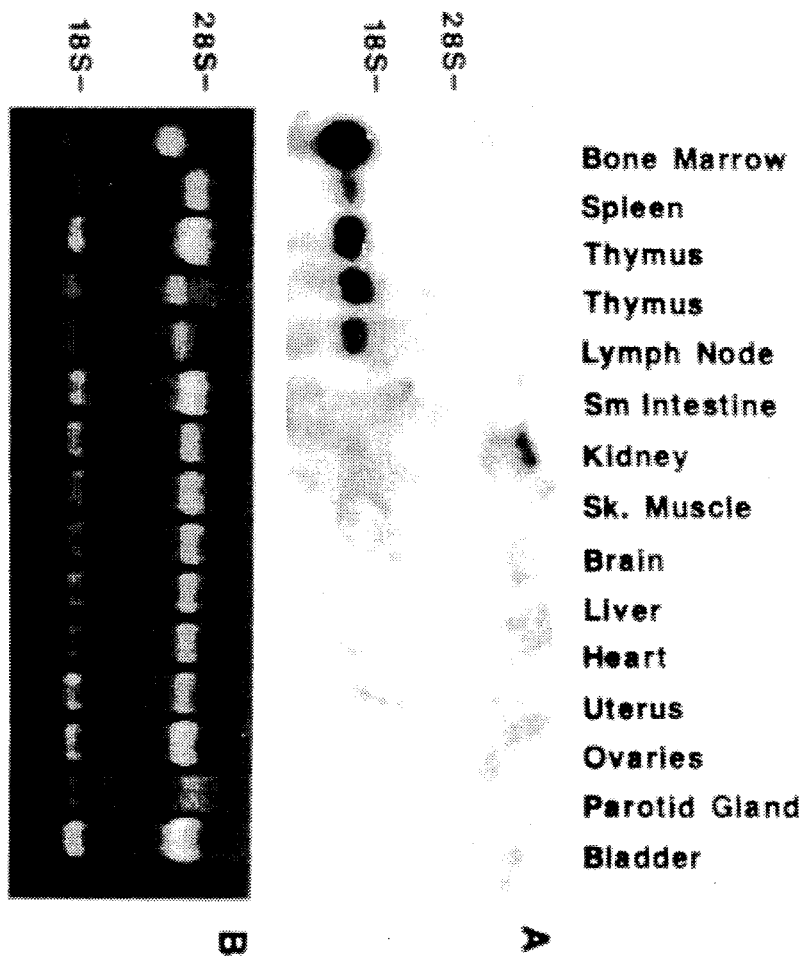
FIGS. 4A and 4B are a Northern analysis of D4 in RNAs (15 μg/lane) extracted from normal murine tissues.

Total RNAs from various normal human tissues was examined to compare with the results from cell lines, as shown by FIG. 3. Human RNAs, except bone marrow, T-lymphocytes and skin fibroblasts, was a kind gift of Dr. B. Seizinger (Massachusetts General Hospital, Boston). Bone marrow cells and peripheral blood T lymphocytes expressed a high level of the transcript. In contrast a weaker signal was seen in the lung while a significantly lower level was seen in other non-hematopoietic tissues, including kidney, liver, adrenal and muscle. A barely detectable signal was seen in brain cells and no transcript was detected in skin fibroblasts. Examination of RNAs from murine tissues with the human CDNA also detected a strongly hybridizing 1.5 kb transcript expressed almost exclusively in hematopoietic tissues, as shown by FIG. 4. These included bone marrow cells, spleen, thymus and lymph nodes.

Molecular characterization of human D4.

Sequence ID No. 3 is the nucleotide sequence and Sequence ID No. 4 is the deduced amino acid sequence of clone D4. The amino acid sequence of the longest open reading frame is shown numbered from the presumed initiating methionine. The TGA stop codon (END) is followed by a 3' untranslated region containing an AATAAA poly(A) addition sequence (underlined). The in-frame upstream stop codon, TAG, is at position 66. The consensus N-glycosylation sites (N-X-S/T) are at nucleotides 594–602 and 648–656.

The cDNA contains putative open reading frame encoding a protein of 201 amino acids with a calculated molecular weight of 23 kd. This is consistent with the preliminary observation of a 23 kd to 24 kd protein obtained by expression of the cDNA in bacteria. Analysis with the Kyte-Doolittle algorithm (Kyte J., Doolittle R. F. (1982) J. Mol. Biol. 157:105–132) revealed the protein to be markedly hydrophilic in its overall characteristic with no hydrophobic domain indicative of a membrane spanning region. A search in the Genbank data base, using the FASTA program ((Pearson W. R., Lipman D. J. (1988) Proc. Natl. Acad. Sci. 85:2444–2448), revealed that clone D4 bears some homology to the bovine rhoGDI cDNA (Fukumoto, et al. (1990) Oncogene 5:1321–1328). They share a 60% identity at the nucleic acid level while the predicted protein sequences are 67% identical. The homology is distributed throughout the cDNA. The greatest divergence is seen within the first 25 amino acids where identical residues dropped to 16%. No significant homology to other genes, particularly other regulators of G-proteins, was identified.

Expression of D4 during differentiation of ES cells.

The regulation of the D4 gene expression during the transition of uncommitted embryonic cells into hematopoietic cells was studied to examine the expression of D4 during the earliest events of hematopoiesis. An in vitro system (Wiles M. V., Keller G. (1991) Development 111:259–267; Schmitt R. M., Bruyns E, Snodgrass H. R. (1991) Genes & Development 5:728–740) whereby murine ES cells, cultured in semi-solid culture conditions, undergo development from single cells into large colonies containing hematopoietic cells of the erythroid, granulocytic and megakaryocytic lineages. Colonies at different days after culture were harvested and total RNA extracted. In a typical experiment, colonies at day 9–10 will display hematopoiesis most easily recognized under inverted light microscopy by a dense ring of erythroid cells mixed with non-erythroid cells or a central core of blood island.

Figures 6A, 6B, 6C, 6D, 6E:
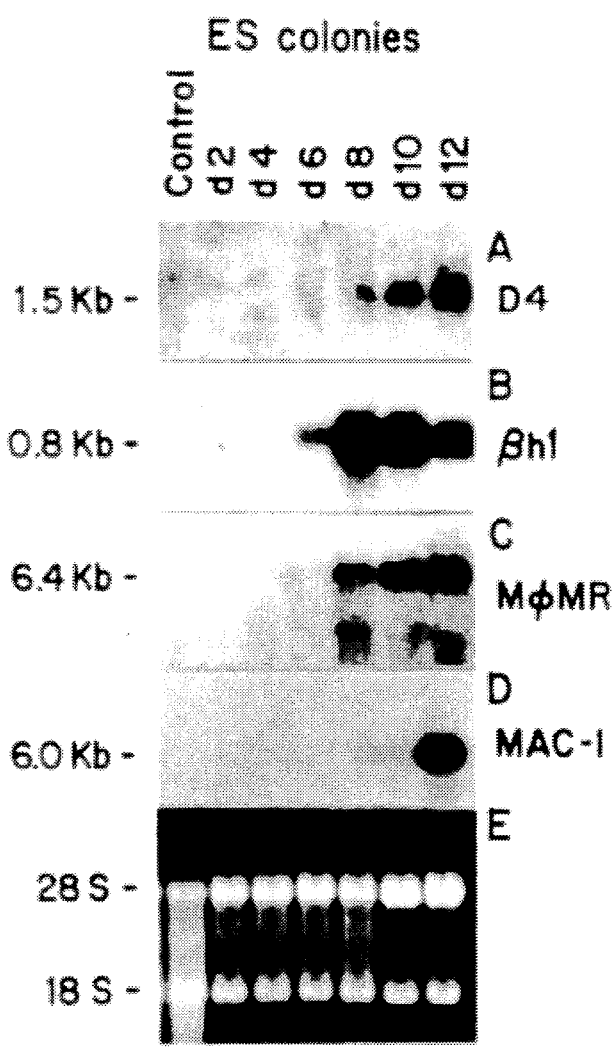
FIGS. 6A, 6B, 6C, 6D, and 6E is a Northern analysis of (A) D4, (B) embryonic globin βh1, (c) murine macrophage mannose receptor MØMR and (D) MAC-1 in RNAs of ES colonies pooled and collected after different days in culture for hematopoietic differentiation. The same blot was probed sequentially A–D. (E) Is an ethidium bromide picture of the gel.

FIG. 6 shows a Northern blot of a panel of RNAs from colonies at days 2, 4, 6, 8, 10 and 12. The filter was probed for D4 and mRNA of several other genes indicative of development along different hematopoietic lineages; embryonic globin βh1 for primitive erythropoiesis (Whitelaw E, Tsai S. F., Hogben P, Orkin S. H. (1990) Mol. Cell. Biol. 10:6596–6606), Mac-I (an integrin cell surface antigen) for mature granulocytes and macrophages (Miller L. J., Schwarting R., Springer T. A. (1986) J. Immunol. 137:2891–2895) and the macrophage mannose-receptor MØMR, specific for macrophage lineage (Stahl P. D. (1990) Am. J. Respir. Cell Mol. Biol. 2:317–318). At day 6, before erythroid cells were recognizable in the colonies, transcripts for βh1 globin were clearly detected. MØMR and D4 transcripts were first detectable between day 6 and 8. Mac-I transcripts were first detected at day 10 and increased strongly by day 12.

Expression of D4 during induced differentiation of hematopoietic cell lines.

Figure 7A:
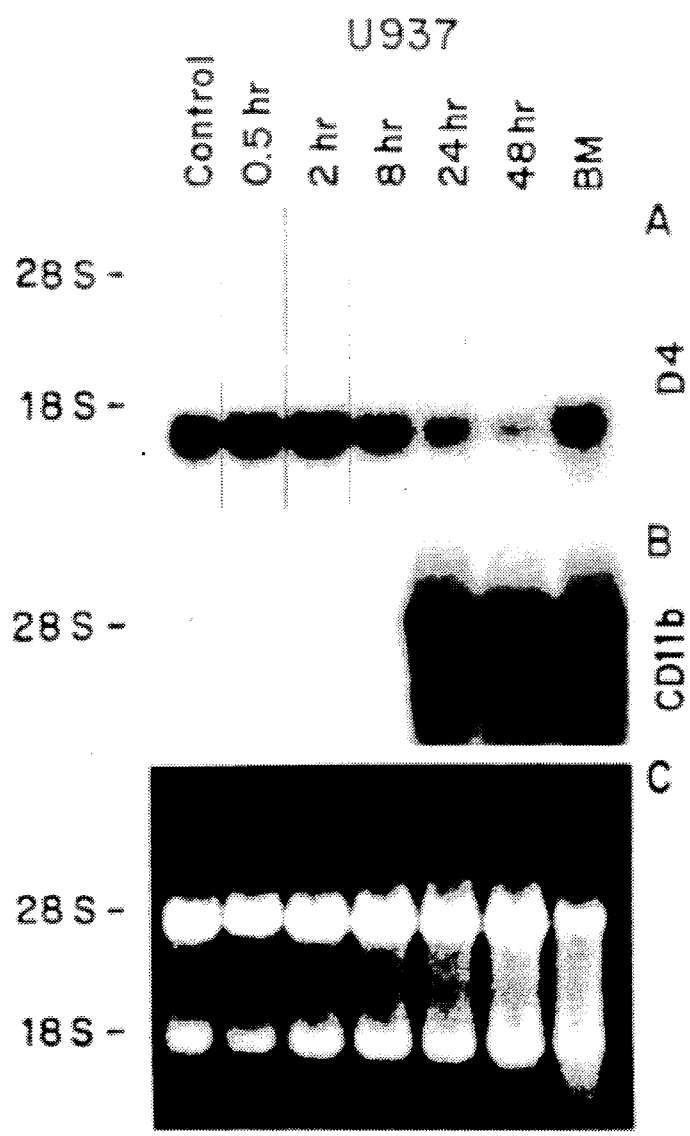
FIGS. 7A–7C is a Northern analysis of hematopoietic cell lines at different times after initiation of induction, control, 0.5, 2, 8, 24, and 48 hr.
Figure 7B:
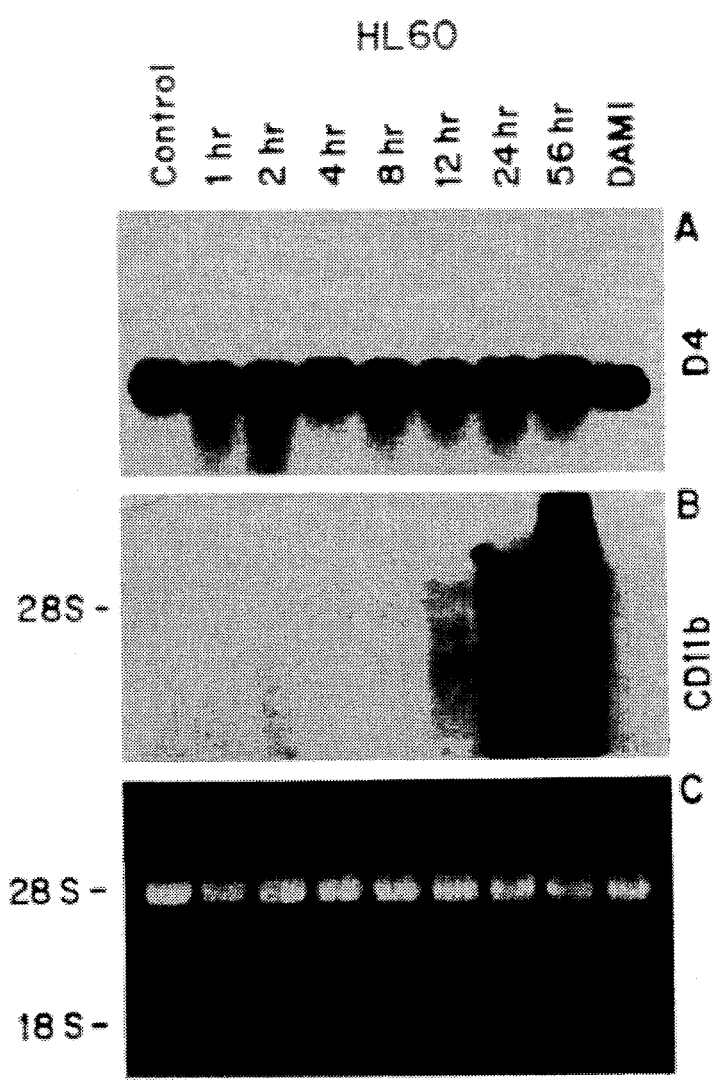
Figure 7C:
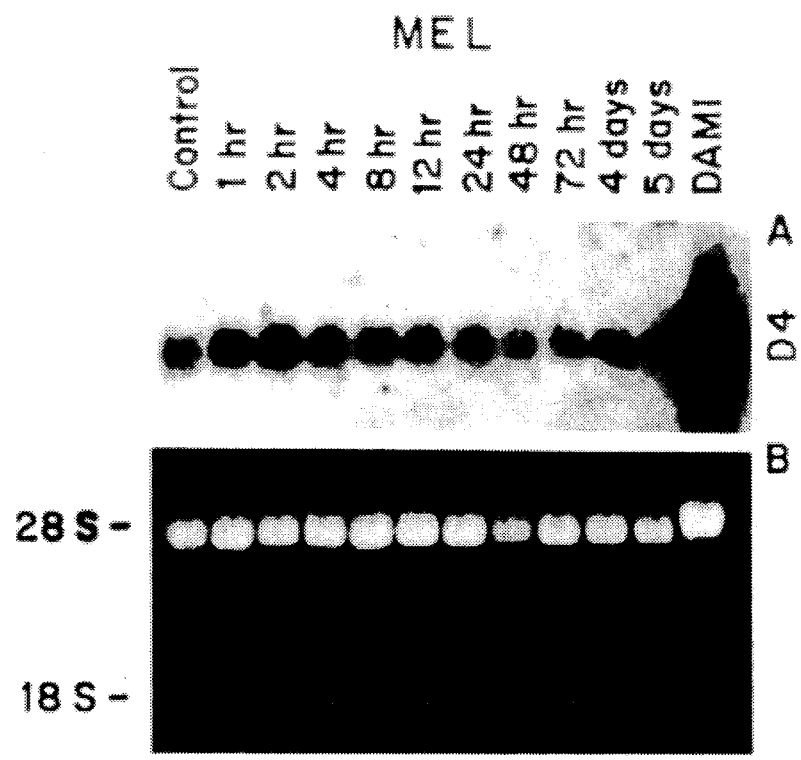

Evidence of modulation of D4 expression during differention was monitored as a further evaluation of the biological function of D4 in hematopoietic cells. Several cell lines representative of various lineages were used in induction experiments. FIGS. 7A, 7B and 7C shows that different lineages are modulated differently as a result of induction. In U937, a myelomonocytic cell line, the induction of differentiation into macrophages by TPA caused a down regulation of D4 so that by 48 hours only a very low level of D4 was detected (FIG. 7A). This was in contrast with the activation and up-regulation of CD11B, the human homologue of Mac-1. When HL60 cells were induced to differentiate into neutrophils (monitored by CD11b expression), no noticeable change in the level of D4 (FIG. 7B) was seen. However, when HL60 cell were induced to differentiate into macrophages using TPA, a down regulation of the transcript was observed as in U937 cells. When the murine erythroleukemia cell line, MEL, was induced to undergo terminal differentiation by DMSO, a strong and rapid up-regulation of D4 was evident within the first 2 hours (FIG. 7C). Differentiation of the MEL cells were indicated by over 80% benzidine positive cells and the appearance of adult, β-globin transcripts.

Isolating murine D4 CDNA.

A total of one million plaques were screened with the human D4 CDNA probe and 11 positive clones were identified. A second round of screening was carried out to isolate 10 individual positive clones. A clone with the longest cDNA insert was selected for sequencing.

Molecular Analysis of murine D4 CDNA.

Sequence ID No. 5 is the nucleotide sequence and Sequence ID No. 6 is the predicted amino acid sequence of the murine D4 1107 bp cDNA clone isolated by the human D4 clone. Computer analysis shows that at the nucleotide level, the human and murine cDNAs are about 82% identical. The cDNA contains an open reading frame encoding a protein with 200 amino acids.

FIG. 5 shows a comparison of the murine and human D4 protein with the bovine rhoGDI (Fukomoto, et al., 1990). There is a high degree of conservation from mouse to man, the proteins being almost 90% identical with the similarities evenly distributed through the protein. As a result, one could obtain with routine efforts the same gene from any other mammalian source. This contrasts with a much lower similarity (67%) between human D4 and bovine rhoGDI. As in the human D4, the greatest divergence between murine D4 and rhoGDI is in the first 20 amino acids.

Expression of D4 in differentiating early hematopoietic cells.

Figure 8A:
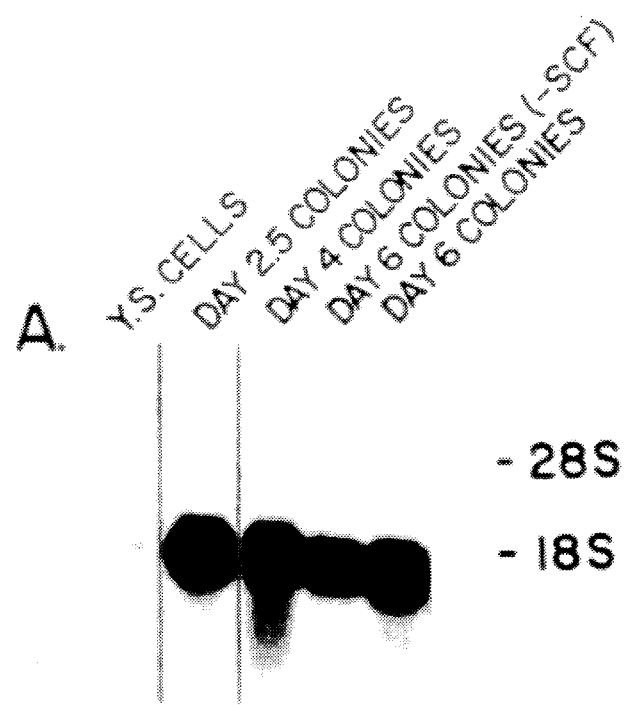
FIGS. 8A and 8B are a Northern analysis of D4 MRNA in total RNA from day 9 murine yolk-sac cells and hematopoietic cells developing in colonies derived from precursor cells after different days in in vitro cultures.
Figure 8B:
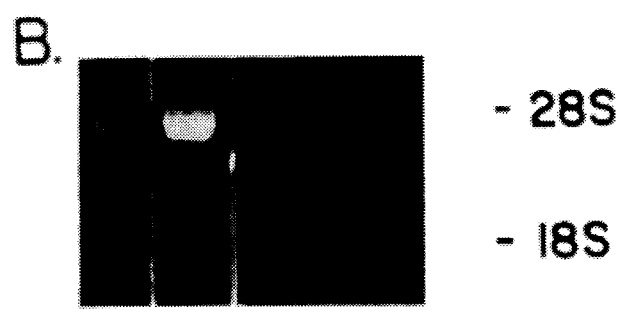

During murine embryogenesis, the earliest site of hematopoietic activity is in day 7 extra-embryonic yolk sac. At day 9 it is possible to dissect away the yolk sac from the embryo and isolate the cellular contents. FIG. 8 demonstrates that the expression of D4 is easily detected in Yolk Sac cells (Y.S. cells) at day 9 gestation. In vitro cultures of this population gave rise to colonies which were collected at days 2.5, 4 and 6. Colony size increased rapidly from 50–100 cells per colony at day 2.5 to about 1000 cells per colony by day 6. At this stage the colonies were a mixture of erythroid, non-erythroid and mixed colonies, similar to what was described by Wong et al (1986) Proc. Natl. Acad. Sci.83:3851–3854, then the colonies stopped expanding and began to degenerate. There was a tremendous increase in the expression of D4 within 2.5 days of culture. This heightened activity appeared to be maintained throughout further development of the progenies within the colonies.

Chromosomal mapping.

The mapping of D4 using the FISH technique shows that it localized to chromosome 12p. A careful analysis of the region revealed that D4 localizes to 12p 12–13.

Examination of both cell lines and normal tissues showed that D4 is expressed at a high level only in hematopoietic cells and is highly conserved across species. This suggests that D4 has some unique functional significance in hematopoietic cells.

Supportive evidence was obtained by examining the expression of D4 during early hematopoiesis in murine ES cells and during differentiation in inducible hematopoietic cell-lines. ES cells are totipotent embryonal cells capable of developing into every tissue type of the animal (Bradley et al., (1984) Nature 309:255–256). The CCE cell line was maintained in liquid cultures as undifferentiated cells in the presence of LIF. Using the in vitro methyl-cellulose culture system described, individual cells developed into mixed-colonies containing erythrocytes, granulocytes and megakaryocytes. The expression of globin genes in these colonies mimic the temporal pattern of embryonic, fetal and adult globin-gene activation in developing embryos (Wiles, et al., (1991); Lindenbaum M. H., Grosveld F. (1990) Genes & Development 4:2075–2085). Colonies from such in vitro cultures of ES cells, containing targeted disruption of the GATA-1 gene, displayed an abrogation of erythroid cell development similar to what was observed in transgenic animals generated by the same mutated ES cells (Simon, et al., (1992) Nature Genetics 1:92–98). Therefore the assay provides a useful alternative to in vivo studies of the expression and function of specific genes during hematopoietic cell development.

The kinetics of D4 expression in these colonies was compared to the expression of three other hematopoietic specific genes, βh1, MØMR and Mac-I, as markers of embryonic erythroid, macrophage and mature granulocytic differentiation. βh1 transcripts were detected the earliest, followed by MØMr and D4. Mac-I was detected at later stage colonies, reflecting the emergence of mature neutrophils and macrophages in the colonies. Therefore it appears that as early hematopoietic cells develop from embryonic cells, D4 is activated. The difference between embryonic hematopoiesis and definitive adult hematopoiesis is still unclear. That D4 transcripts were seen after the initiation of embryonal globin transcription suggests that D4 might not be relevant during embryonic hematopoiesis or at least not during embryonic erythropoiesis.

D4 expression in a population of primitive progenitors was determined to provide further evidence of the significance of D4 in early hematopoiesis. The first site of hematopoietic activity is in day 7 yolk sac where the cell population consist largely of primitive erythroblasts. A second wave of stem cells and progenitors develops which migrate to the fetal liver to initiate hepatic hematopoiesis. By day 9.5 to 10.5 the liver contains stem cells capable of reconstituting adult hematopoiesis. The cells in day 9 yolk sac can be physically isolated. Wong et al has demonstrated a high frequency of single- and multi-lineage precursors within this population. In contrast, cells from the embryo proper at day 9 do not harbor colony-forming cells. Lui et al has also shown that the day 9 yolk sac cells contain T cell precursors that could reconstitute fetal thymus. Such results indicate that the yolk sac is the source of stem cells that migrate to seed the adult hematopoietic tissues. D4 transcripts were easily detected in day 9 yolk sac cells. Furthermore, when hematopoietic progenitor cells from the yolk sac were allowed to differentiate in vitro into colonies, a dramatic increase in the level of D4 expression was seen. These results together indicate that the D4 protein is essential during the earliest phases of hematopoietic cell development.

Hematopoietic cell lines induced to undergo differentiation revealed markedly different regulation of D4 expression. During differentiation into macrophages, D4 transcripts became significantly down regulated. In contrast, differentiation into neutrophils showed no obvious change in the level of D4 expressed while differentiation along the erythroid lineage caused a very early transient increase followed by a fall to base-line level.

Taken together, these results suggest that D4 is involved in the regulatory processes of adult hematopoiesis and that it may function differently in different lineages.

Generation of human D4 fusion protein.

Figure 9A:
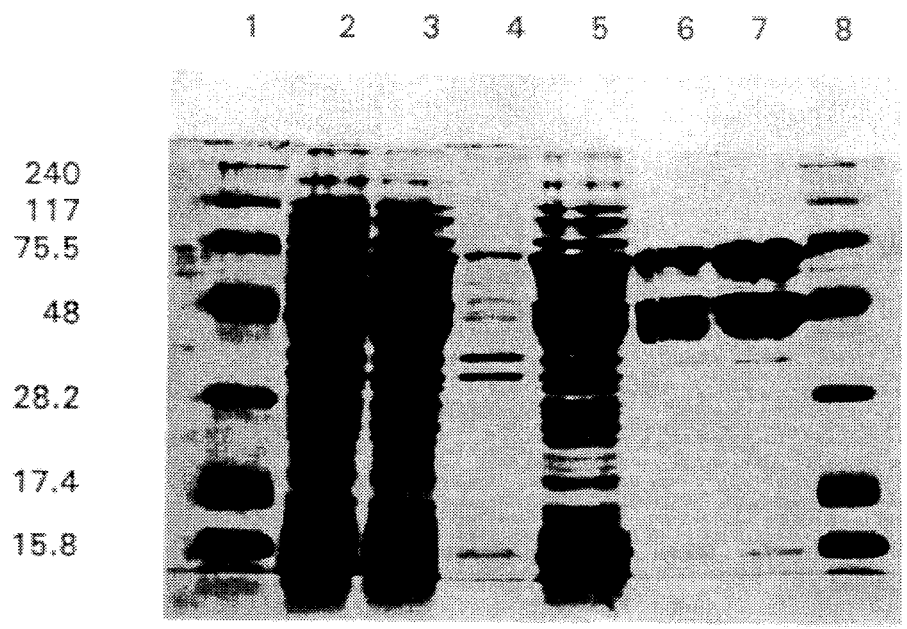
FIGS. 9A and 9B are SDS PAGE profiles of purification steps for the malE-D4 fusion protein expressed in E. coli.
Figure 9B:
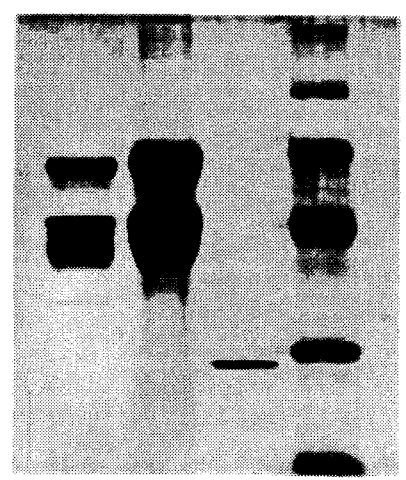

FIGS. 9A and 9B show the production in bacteria of a fusion protein of the predicted molecular weight of 71 Kd. The purification of the fusion protein was followed by the cleavage of the mal-D4 protein with thrombin. Final separation of the pure iD4 protein was achieved by passage through an amylose column giving rise to the expected iD4 protein of molecular weight 24 kd.

Assay for GDI and GDS activity of D4.

The murine cDNA for D4 and the predicted protein is 89% identical to the human protein. The data presented here show that the murine D4 is almost 90% identical to the human protein. D4 and rhoGDI are 67% homologous and are therefore most likely members of a family of GTP-binding protein regulators. In searching for GDIs for CDC42, Leonard et al (1992) J. Biol Chem. 267(12), 22860–22868, have recently isolated and purified a protein which acts as a strong GDI for CDC42. Based on cyanogen-bromide-generated sequence, the CDC42-GDI appears to be very similar, if not identical to, the rhoGDI. In addition, a common GDI appears to couple to the rac 1 protein (as well as to rho and CDC42Hs). Given the sequence similarity between D4 and the rho-subtype GDI, the iD4 protein was tested for GDI activity.

Figure 10A:
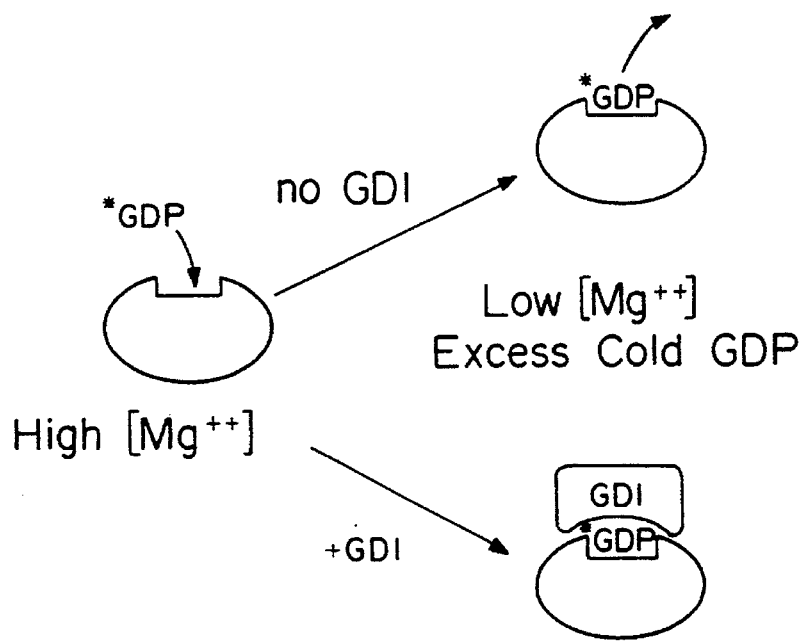
FIGS. 10A, 10B, 10C and 10D are assays for GDI activity in D4.
Figure 10B:
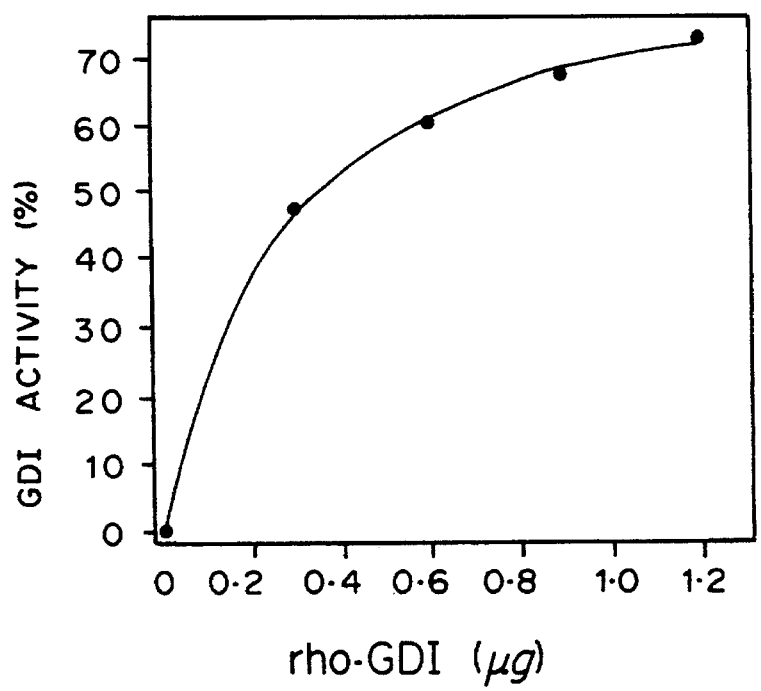
Figure 10C:
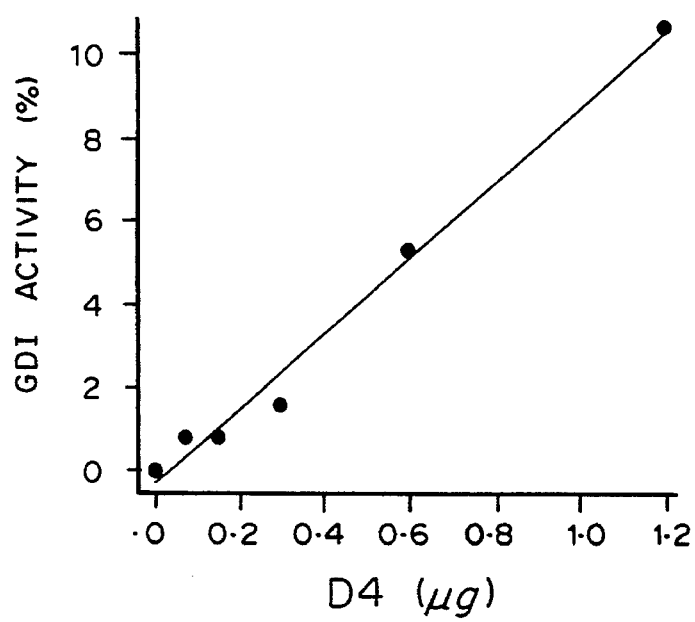
Figure 10D:
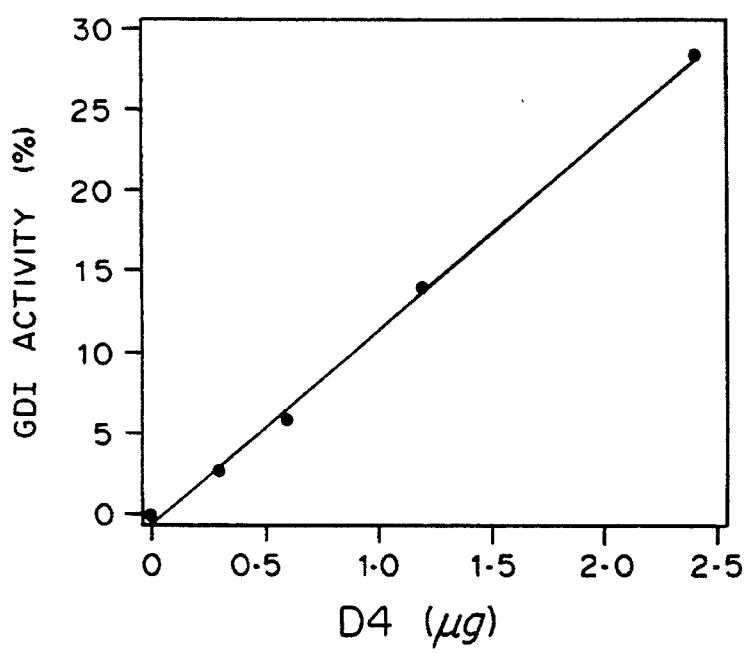

The principle behind the assay is shown in FIG. 10A. FIGS. 10B, 10C and 10D show that D4 exerts a low level of GDI activity against CDC42 and rac 1. Compared to an equivalent quantity of rhoGDI, it was estimated that D4 has only about 5–10% of the GDI activity against the target G-proteins. The dose response profiles indicate that D4 binds significantly more weakly but has activity has a GDI.

GDIs, by virtue of their function, are rate limiting factors in the generation of activated G-proteins and are therefore potential tumor suppressors. In this context, the mapping of D4 to chromosome 12p 12–13 is relevant. A significant percentage of acute leukemias contain either deletions or translocations involving this region. Deletions of 12p 12–13 in acute leukemias have been described by Carroll, et al., (1987) Blood 70:1962–1965. A non-random t(4;12p12) translocation has also been described by Raimondi, et al., (1991) Blood 77:2016–2022). Since D4 has GDI activity, it is possible that D4 is involved in leukemogenesis. Further understanding of the significance of D4 in hematopoietic cells can be gained by examining the affect of D4 mutations and deletions in cell lines and animals.

A comparison of the sequence of murine and human D4 shows that the similarity with rhoGDI is distributed across the molecule. The greatest divergence is in the first 20 or so amino acids. Despite this similarity, the functional studies of D4 show that it is capable of exerting GDI activity at a level many times lower than rhoGDI against the same target GTP binding protein, CDC42Hs and rac 1. There are two possible explanations. It is possible that D4 is a GDI for one of these known molecules. For example, rac 2 is specifically expressed in myeloid cells and lymphoid cells. However, rac 2 is almost identical to rac 1, differing only by a few amino acids. It is very doubtful that D4 will exhibit a more significant GDI activity against rac 2. Rho and rhoGDI are expressed widely, and in more or less the same levels, in most hematopoietic and non-hematopoietic cells. In contrast, D4 is clearly preferentially expressed at very high levels in hematopoietic cells. Thus, it seems unlikely that D4 acts as a redundant GDI for rho. Finally, there is no similarity at all between D4 and the smg25(rab) GDI. As a result, it is believed that D4 is either a GDI for an as yet unknown GTP-binding protein or that the real in vivo function of D4 is not the inhibition of GDP dissociation.

Clinical, Diagnostic and Research application.

D4 has properties of a GDI and is preferentially expressed in hematopoietic cells. As a GDI, D4 should play a key role in regulating the activity of these GTP-binding proteins. The current view is that GDIs, among other cellular functions, are potential tumor suppressors. Physiologically, GDIs, such as D4, are crucial in the proper control of cell division and differentiation. The identification of these molecules opens up an area accessible to therapeutic intervention (Marx J. (1992) Science 257:484–485). Available information indicates that D4 very likely plays an important role in the differentiation and proliferation of hematopoietic cells and perhaps in a few other tissues as well, such as brain, pre-adipocytes, muscle cells, melanocytes, lung and prostate.

The super family of ras related small GTP-binding proteins, as described in more detail below, are involved in a wide range of important cellular functions. D4 could also turn out to be an important regulator of different normal physiological functions of a specific lineages.

The Super Family of ras/ras-like Genes ras Gene:

Genes of the ras family (H, K and N-ras) were first identified as transforming genes in human tumors by Barbacid M. (1987) Ann. Rev. Biochem. 56:779–827. The high degree of conservation of ras genes throughout eukaryotic evolution indicates that they very likely have a fundamental role in basic cellular functions. The ras proteins are similar to adenylate cyclase G-proteins in binding GTP, having GTPase activity and localizing to the inner leaflet of the plasma membrane, Kaziro Y., et al. (1991) Annual Review of Biochem 60:349–400. Much evidence indicates that the ras gene products participate in transducing across cellular membranes signals that regulate cell division, Hall A. (1992) Cell 69:389–391; McCormick F. (1989) Cell 56:5. Its implication in leukemogenesis is substantiated by the discovery of ras mutations in MDS, Hirai H., et al., (1987) Nature 327:430–432, and acute leukemias, Bos, et al., (1985) Nature 315(27):726–730.

rho, ras-related gene family:

Recently, another class of ras-related genes has been identified, adding further complexity to the research on ras. This new gene family, denoted rho for ras homology, encodes proteins that share 35% amino acid homology with ras, Madaule P, Axel R. (1985) Cell 41:31–40. Three highly homologous members of the rho family, A, B and C, have been identified. The rho proteins exist widely in various species, from yeast to man, as described for ras p21s, Madaule P, Axel R, Myers AM. (1987) Proc. Natl. Acad. Sci. USA 84:779–783. As in ras, rho is highly conserved evolutionarily, with the aplysia (snail) rho and human rhoA sharing 85% protein identities, Madaule P, Axel R. (1985) Cell 41:31–40. Since the discovery of the rho family, several other ras-related G-proteins have been identified, all with the Ras canonical boxes. They can be divided into four major groups based on protein sequences: (i) the ras group that includes the proto-oncogenes H-, K- and N-ras (Ellis, et al. (1981) Nature (London) 292:506–511; Lows, et al. (1987) Cell 48:137–146), ral (Chardin P., Tavitian. (1986) EMBO J. 5:2203–2208), and rap (Pizon, et al., (1988) Oncogene 3:201–204) genes, (ii) rab or YPT group (Touchot N., Chardin P., Tavitian A. (1987) Proc. Natl. Acad. Sci. USA 84:8210–8214), (iii) the rho group which includes CDC42, rac I and II, and TC10 (Vincent S., Jeanteur P., Fort P. (1992) Molecular and Cellular Biology 12(7):3138–3148), and (iv) TC4 (Drivas, et al., (1990) Mol. Cell. Biol. 10:1793–1798).

The functions of these ras-related proteins remain unclear. Several experiments have illustrated the striking effect rho proteins have on cellular functions. Disruption of yeast rho 1 gene is lethal for the microorganism (Madaule and Axel (1985) Cell 41:41–40). Overexpression of the rho A gene in fibroblasts reduces serum dependence for cell growth and is tumorigenic in nude mice (Avraham H., Weinberg R. A. (1989) Mol. Cell Biol. 9:2058–2066). Ribosylation of rho proteins by ADP-ribosyltransferase C3 induces morphological changes of several types of cells through microfilament disassembly, as reported by Chardin, et al. (1989) EMBO 8:1087–1092; Ridley A. J., Hall A. (1992) Cell 70:389–399. More recently, Ridley et al have shown, by injection of rho and rac protein into fibroblasts, that rho controls the formation of stress fibers (Ridley, et al. (1992) Cell 70:401–410), while rac causes the ruffling of cells (Trahey, et al. (1988) Science 242:1697–1700). Thus, it is apparent that rho proteins are involved in the regulation of cytoskeletal organization and cell morphology. The whole family of rho related proteins contain several domains with stretches of identical residues, as reviewed by Vincent S., Jeanteur P., Fort P. (1992) Mol. Cell. Biol. 12(7):3138–3148.

Regulators of GTP-binding/GTPase cycles of ras-related G-proteins.

Figure 11:
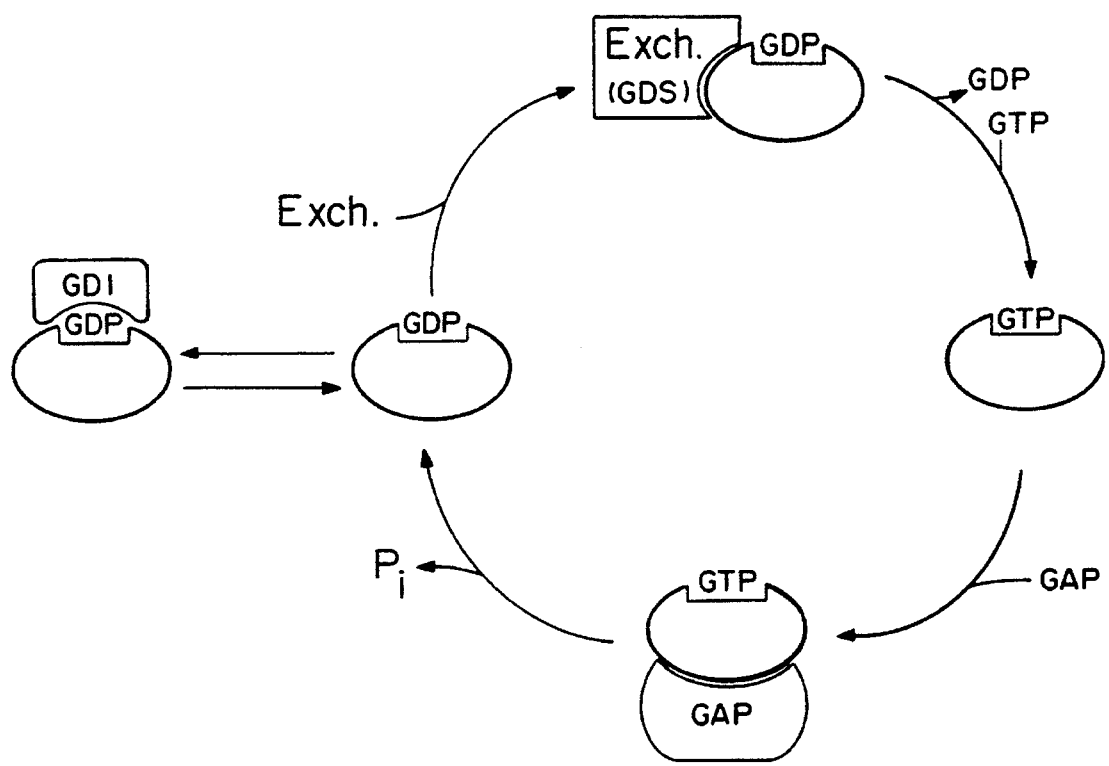
FIG. 11 is a schematic depiction of GDI in inhibition of GDP dissociation from the GTP-binding protein, 'G'. An active GTP-bound form is generated from the inactive GDP-bound form by nucleotide exchange catalyzed by GDS, the GDP-dissociation stimulator. The GTPase activating protein, GAP, increases the inherent GTPase activity of the 'G' protein by several hundred fold, and converts the active GTP-bound form into the inactive GDP-bound form again through hydrolysis of the GTP.

The small G-proteins bind to guanine nucleotides (GTP and GDP) and possess low intrinsic GTPase activity. Three classes of regulators are recognized so far, as depicted in FIG. 11: the GTPase-activating proteins (GAPs), stimulators of GDP dissociation (GDS) and the inhibitors of GDP-dissociation (GDI). Several such regulators have been isolated for different members of the ras-super family. It turns out that ras-GAP (Trahey, et al. (1988) Science 242:1697–1700; Vogel, et al., (1988) Nature 335:90–93), is a member of a family of GAPs with a highly conserved domain and include the neurofibromatosis(NF1) gene product (McCormick F. (1989) Cell 56:5), the yeast IRA proteins (Tanaka, et al., (1990) Cell 60:803–807), and GAP 1 (Imai, et al., (1991) Mol. Cell. Biol. 11, 3088–3094). Another group of GAPs is linked by a different homologous domain, including rhoGAP, chimerin, PI-3 kinase subunit p85a,b (Garrett, et al., (1989) J. Biol Chem 264:10–13). Similarly, a family of GDS exists: DBL (Borzillo, et al., (1990) Mol. Cell Biol. 10:2704–2174), VAV (Katzav, et al. (1989) EMBO Journal 8:2283–2290), and LBC, recognized by a homologous domain required for transformation in hematopoietic cells. Two GDI have been described so far, rab3/smgp25a-GDI (Matusui, et al., (1990) Mol. Cell. Biol. 10:4116–4122), and rho-GDI (Ueda, et al., (1990) J. Biol. Chem. 265:9373–9380; Fukumoto, et al., (1990) Oncogene 5:1321–1328), and there are no similarities between them.

Biochemical connection between ras and other ras-related proteins.

Ras and ras-like proteins interact through complex molecules with multiple functional G-protein-interacting domains. The cDNA for the rasGAP-binding protein pl 90 (Ellis, et al., (1992) Nature 343:377–381), was cloned recently and found to have a GTP-binding domain, a transcription repressor domain and the rhoGAP homologous domain (Settleman, et al., (1992) Cell 69:539–549). BCR is a large pl 60 protein with a novel serine-kinase domain (Maru Y., Witte O. N. (1991) Cell 67:459–468), a dbl-homologous domain(GDS) (Ron, et al., (1991) New Biol. 3:372), and a rho-homologous GAP for p21rac (Diekmann, et al., (1991) Nature 351:400–402). The recently cloned rasGDS has the CDC25 homologous GDS domain in the C-terminus while the amino end contains the dbl-homologous domain (Shou (1992) Nature 358:351–354). Common to many of these are the SH2/SH3 motifs (e.g. in vav, rasGAP, PI-3 kinase subunit) believed to be important for the linking of activated receptors to downstream signals (Koch, et al., (1991) Science 252:668–674; Hall A. (1990) Science 249:635–640; Puil L., Pawson T. (1992) Cell Regulation 2:275–277).

At the moment, however, one can only speculate that an intimate biochemical relation exists between the ras super-families, with ras predominantly controlling the cell cycle and the rho-family of protein regulating cell morphology and other physiological functions. However, there is increasing evidence pointing toward many critical roles played by the super-family of ras-related small GTP-binding proteins in the cellular differentiation, proliferation and functions of a wide range of tissues. Regulators of the active state of G-proteins are therefore critical molecules. This importance is underscored by increasing evidence implicating them in clinically important diseases. The dbl proto-oncogene, identified initially as an oncogene in a human B-cell lymphoma, is a guanine nucleotide exchange factor for the ras-related protein, CDC42Hs (Hart, et al., (1991) Nature 354:311–314). Bcr, the breakpoint cluster region gene involved in chronic myeloid leukemia, encodes a multi-functional protein that include a dbl-homologous domain (Ron, et al., (1991) New Biol. 3:372), and a domain for activating GTPase activity (GAP) of p21rac (Diekmann, et al., (1991) Nature 351:400–402). Neurofibrin (NF1), the neurofibromatosis type 1 susceptibility gene, is a GAP protein for p21ras (Bollag G., McCormick F. (1992) Nature 356:663–664).

The preferential expression of D4 in blood cells is indicative of a gene with unique and functional significance in hematopoietic cells. It is interesting to note that vav (Katzav, et al., (1989) EMBO Journal 8:2283–2290), a proto-oncogene expressed specifically in all hematopoietic lineages, contains a region sharing homologies with the GDP/GTP exchange domain of dbl, CDC24 and bcr (Adams, et al., (1992) Oncogene 7:611–618). These proteins may represent a related family of positive regulators acting as catalysts for the dissociation of GDP from G-proteins in different tissues. It is very likely that a group of GDP-dissociation inhibitors, such as rhoGDI and possibly D4, function as negative regulators of G-protein activation. The determination of the biochemical action of D4 is therefore of great interest and expected to be very important in the role cancer and cell differentiation, especially of hematopoietic cells.

Diagnostic Application i) Leukemia.

D4 cDNA can be used to analyze RNA and DNA from leukemic patients, particular those with chromosomal abnormalities involving chromosome 12p 12–13 region, and other diseases suspected to involve D4. RNAs will be examined for missing or aberrant transcripts of D4 and DNAs will be examined for rearrangements of the D4 gene. This will help scientists and clinicians determine if there is a sub-type of leukemia due to abnormalities of the D4 gene or its expression.

Other Diseases.

Other useful areas of diagnostic application include studies of diseases of tissues where D4 is expressed but at a low level, including lung, skin (melanocytes), prostate, muscle, kidney, ovaries, bladder, fatty and neuronal tissue.

The D4 cDNA can be used in diagnosis using standard techniques. In most cases, it is necessary to use only short sequential sequences of the cDNA or gene, ranging from seventeen to thirty oligonucleotides in length. The RNA can also be used. The nucleic acid can be screened for hybridization as described above or labelled with a dye, fluorescent molecule, radiolabel or enzyme for detection, or immobilized and used in that manner for screening.

Clinical Application

Use of the Protein i) Treatment of leukemia and Other Diseases.

In those diseases where the D4 gene is defective or the protein missing, D4 will be administered into, or the D4 gene introduced into, the cells where the protein is missing or defective. Although the delivery of specific proteins into cells is still a major obstacle in the use and application of many proteins which could now be produced in industrial scale if necessary, several methodologies are being explored to achieve intra-cellular delivery of intact proteins. These methodologies include:

a) Polyethylene Glycol (PEG)-modified protein. The technique is based on the principle of increasing the plasma half-life and reducing the immunogenicity of circulating protein by a covalent conjugation of the protein to PEG. The best example is the successful treatment of patients with the Adenosine Deaminase (ADA) enzyme deficiency disease, a Sub-acute Combined Immunodeficiency (SCID), with the PEG-ADA, as reported by Hershfield, et al., (1987) New Eng. J. Med. 316:589–596. This has encouraged exploration of more versatile uses of PEG such as conjugation to growth factors (Tanaka, et al., (1991) Cancer Research 51:3710–3714), antibodies (Kitamura, et al., (1991) Cancer Research 51:4310–4315), chemotherapeutic agents and modifying proteins to increase additional sites for PEG attachment (Hershfield, et al., (1991) Proc. Natl. Acad. Sci. USA 88:7185–7189).

b) Liposomes. The use of liposomes to deliver drugs and macromolecules to tissues in vivo is being intensely pursued, as reported by Ostro, M. J., ed. (1989) Liposomes from Biophysics to Therapeutics (Dekker, New York) pp. 1–369; Gregoriadis, G. ed. (1988) Liposomes as Drug Carriers (Wiley, New York), pp. 1–863. The method has the potential of delivering a wide range of drugs and macromolecules, including recombinant proteins. Modifications of the lipid composition have generated carriers that not only avoid rapid uptake by the reticulo-endothelial system but can be targeted to certain tissues (Papahadjopoulos, et al., (1991) Proc. Natl. Acad. Sci. USA 88:11460–11464; Maruyama K., Kennel S., Huang L. (1990) Proc. Natl. Acad. Sci. USA 87:5744–5748; Hughes B. J., Kennel, Lee R., Huang L. (1989) Cancer Research 49:6214–6220). In vivo trials have also demonstrated the feasibility of clinical applications, as reported by Lopez-Berestein, et al., (1985) J. Inf. Dis. 151:704–710.

c) Receptor-mediated endocytosis of toxins, such as diphtheria and preudomonas toxin conjugated to natural ligands such as polypeptide hormones, has been exploited successfully to deliver macromolecules to certain cells, as reported by Vitetta, et al., (1987) Science 238:1098–1104; Pastan, et al., (1986) Cell 47:641–648. This methodology is being explored further to expand the repertoire of potential target tissues. An example is the recently described use of the endocytosis of folate-conjugated proteins, through the folate receptor present and active in all dividing cells, to deliver large number of intact macromolecules (greater than $10^8$ copies) into cells, as reported by Leamon C. P., Low P. S. (1991) Proc. Natl. Acad. Sci. USA 88:5572–5576.

If a sub-type of leukemia with an abnormality of the D4 gene is identified, the patient can be treated by providing with or administering to the malignant cells the functional protein. The same methodology can be applied to defects or diseases of other tissues which involves defects in or absent D4.

Use of the cDNA/Gene i) In vitro Amplification of Hematopoietic Stem Cells.

There is substantial preliminary evidence indicating that the need for D4 is greatly increased during the growth and differentiation of very primitive hematopoietic progenitor cells. It is therefore believed that D4 is necessary for the progression of differentiation and that blocking the activity of D4 might stop differentiation but not proliferation.

Currently there is considerable effort being invested to devise a means of harvesting bone-marrow from patients, amplify the number of stem cells (before transplantation) by in vitro culture and stimulation with various combinations of the presently known plethora of hematopoietic cytokines. One of the major problems encountered is that many of the cytokines stimulate division and differentiation at the same time. By blocking the activity of D4 it may be possible to temporarily inhibit the differentiation but not the amplification. One way of achieving this is to block the translation of the protein with antisense oligo nucleotides (Wagner, et al., (1992) Proc. Natl. Acad. Sci. 89:6785–6789; Skorski, et al., (1992) J. Exp. Med. 175:743–750), based on the sequence information of D4. This technique is already moving rapidly into in vivo animal experiments with practical clinical application in the not too distant future, as reported by Bayever, et al., (1992) Blood 80, Suppl 1, Abstract 833.

ii) Gene Therapy.

The replacement of a defective gene in a cell with a normal gene is already being tested in clinical trials, as reported by Miller AD. (1992) Nature 357:455–460. 'Gene therapy' has been successfully achieved for a few cases of SCID patients who are being closely followed. It is expected that this means of therapy will be applicable for a wide range of genetic diseases involving different tissues. A dramatic example is the in vivo transfer of the human Cystic Fibrosis transmembrane conductance regulator gene to the airway epithelium of rats, as reported by Rosenfeld, et al., (1992) Cell 68:143–155.

The D4 cDNA can also be used for gene therapy of disorders involving absent or defective D4 using retroviral vectors (Miller AD. (1992) Nature 357:455–460; van Beusechem, et al., (1992) Proc. Natl. Acad. Sci. 89:7640–7644), adenoviral vectors (Rosenfeld, et al., (1992) Cell 68:143–155; Lemarchand, et al., (1992) Proc. Natl. Acad. Sci. 89:7640–7644), and physical methods of DNA and DNA-complexes transfer via liposomes (Miller AD. (1992) Nature 357:455–460), and transferrin and other cell specific receptors (Zenke, et al., (1990) Proc. Natl. Acad. Sci. USA, 87:3655–3659; Curiel, et al., (1991) Proc. Natl. Acad. Sci. 88:8850–8854; Wu, et al., (1991) J. Biol. Chem. 266:14338–14342).

Research Application i) Use of Specific Antibody.

Rabbits were immunized against the D4 protein. The antibody isolated from the serum is capable of identifying a specific protein band, corresponding to the D4 protein, in hematopoietic cells. The antibody can be used to look for interacting protein(s) that can be identified by the co-immunoprecipitating technique of Settleman, et al., (1992) Cell 69:539–549; and Wong, et al., (1992) Cell 69:551–558. The antibody can also be used for diagnostic purposes, e.g., examination of tissues. A number of screening techniques are well known for the use of antibodies alone, or labelled with a dye, fluorescent label, radiolabel, or enzyme.

ii) Use of the Protein.

The D1 protein can also be used to look for interacting proteins using in situ hybridization techniques which have been successfully used in identifying several important biological molecules, as reported by Blanar M. A., Rutter W. J. (1991) Science 256:1014–1018; LeClair K. P., Blanar M. A., Sharp P. A. (1992) Proc. Natl. Acad. Sci. USA, 89:8145–8149; Cicchetti P., Mayer B. J., Thiel G., Baltimore D. (1992) Science 257:803–806; Kaelin, et al., (1992) Cell 70:351–364.

iii) Animal Models with D4 Defect.

The genomic clone of D4 has been isolated. This can be used to create a gene-targeting vector to disrupt the D4 gene in murine embryonal stem (ES) cells by homologous recombination, using the method of Capecchi M. R. (1989) Science 244:1288–1292; Koller B. H., Smithies O. (1992) Ann. Rev. Immunol. 10:705–730. Such cells can then be used to generate animals that are either heterozygous or homozygous for D4 gene deletion, using the method of Travis J. (1992) Science 256:1392–1394. These animals will serve as excellent models for biological and pharmacological investigations in the field of GTP-binding proteins.

The teachings of the foregoing publications are illustrative of the skill and techniques known to those skill in the art and are not believed to constitute essential information. The teachings of the publications are specifically incorporated by reference.

Modifications and variations of the D4 protein and DNA encoding the protein will be obvious to those skilled in the art from the foregoing detailed description. Such modifications and variations are intended to come within the scope of the claims.

We claim:

1. An isolated nucleic acid sequence encoding all or part of the mammalian D4 protein, at least fourteen to seventeen nucleotides in length, which is distinct from the bovine rhoGDI sequence.

2. The sequence of claim 1 further comprising a label.

3. The sequence of claim 1 wherein the sequence is of human origin.

4. The sequence of claim 1 wherein the sequence is of murine origin.

5. The sequence of claim 3 encoding the amino acid sequence shown in Sequence ID No. 4.

6. The sequence of claim 3 as shown in Sequence ID No. 3.

7. The sequence of claim 4 encoding the amino acid sequence shown in Sequence ID No. 6.

8. The sequence of claim 4 as shown in Sequence ID No. 5.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 33 base pairs
( B ) TYPE: nucleic acid (C) STRANDEDNESS: single
(D) TOPOLOGY: linear (ii) MOLECULE TYPE: cDNA (iii) HYPOTHETICAL: NO (iv) ANTI-SENSE: NO (vi) ORIGINAL SOURCE:
(A) ORGANISM: Homo sapiens (xi) SEQUENCE DESCRIPTION: SEQ ID NO:1:

ATTATGACTG AAAAAGCCCC AGAGCCACAT GTG                    33

(2) INFORMATION FOR SEQ ID NO:2:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (vi) ORIGINAL SOURCE:
(A) ORGANISM: Homo sapiens (xi) SEQUENCE DESCRIPTION: SEQ ID NO:2:

GACTCTAGAT CATTCTGTCC ACTCCTTCTT                         30

(2) INFORMATION FOR SEQ ID NO:3:

(i) SEQUENCE CHARACTERISTICS:
(A) LENGTH: 1171 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (vi) ORIGINAL SOURCE:
(A) ORGANISM: Homo sapiens (ix) FEATURE:
(A) NAME/KEY: terminator
(B) LOCATION: 66..68
(D) OTHER INFORMATION: /note= "In-frame upstream stop
codon."

(ix) FEATURE:
(A) NAME/KEY: misc_feature
(B) LOCATION: 594..602
(D) OTHER INFORMATION: /note= "Consensus N-glycosylation
site."

(ix) FEATURE:
(A) NAME/KEY: misc_feature
(B) LOCATION: 648..656
(D) OTHER INFORMATION: /note= "Consensus N-glycosylation
site."

(xi) SEQUENCE DESCRIPTION: SEQ ID NO:3:

AGTACTCAGA AGTCAGAGTT GAGAGACAGA GGCACCCCGG ACAGAGACGT GAAGCACTGA    60

ATAAATAGAT CAGAATGACT GAAAAGCCC CAGAGCCACA TGTGGAGGAG GATGACGATG    120

|  |  |  |  |  |  |  |
|---|---|---|---|---|---|---|
| ATGAGCTGGA | CAGCAAGCTC | AATTATAAGC | CTCCACCACA | GAAGTCCCTG | AAAGAGCTGC | 180 |
| AGGAAATGGA | CAAAGATGAT | GAGAGTCTAA | TTAAGTACAA | GAAAACGCTG | CTGGGAGATG | 240 |
| GTCCTGTGGT | GACAGATCCG | AAAGCCCCCA | ATGTCGTTGT | CACCCGGCTC | ACCCTGGTTT | 300 |
| GTGAGAGTGC | CCCGGGACCA | ATCACCATGG | ACCTTACTGG | AGATCTGGAA | GCCCTCAAAA | 360 |
| AGGAAACCAT | TGTGTTAAAG | GAAGGTTCTG | AATATAGAGT | CAAAATTCAC | TTCAAAGTGA | 420 |
| ACAGGGATAT | TGTGTCAGGC | CTGAAATACG | TTCAGCACAC | CTACAGGACT | GGGGTGAAAG | 480 |
| TGGATAAAGC | AACATTTATG | GTTGGCAGCT | ATGGACCTCG | GCCTGAGGAG | TATGAGTTCC | 540 |
| TCACTCCAGT | TGAGGAGGCT | CCCAAGGGCA | TGCTGGCCCA | AGACACGTAC | CACAACAAGT | 600 |
| CCTTCTTCAC | CGACGATGAC | AAGCAAGACC | ACCTCAGCTG | GGAGTGGAAC | CTGTCGATTA | 660 |
| AGAAGGAGTG | GACAGAATGA | ATGCATCCAC | CCCTTTCCCC | ACCCTTGCCA | CCTGGAAGAA | 720 |
| TTCTCTCAGG | CGTGTTCAGC | ACCCTGTCCC | TCCTCCCTGT | CCACAGCTGG | GTCCCTCTTC | 780 |
| AACACTGCCA | CATTTCCTTA | TTGATGCATC | TTTTCCCACC | CTGTCACTCA | ACGTGGTCCC | 840 |
| TAGAACAAGA | GGCTTAAAAC | CGGGCTTTCA | CCCAACCTGC | TCCCTCTGAT | CCTCCATCAG | 900 |
| GGCCAGATCT | TCCACGTCTC | CATCTCAGTA | CACAATCATT | TAATATTTCC | CTGTCTTACC | 960 |
| CCTATTCAAG | CAATTAGAGG | CCAGAAAATG | GGCAAATTAT | CACTAACAGG | TCTTTGACTC | 1020 |
| AGGTTCCAGT | AGTTCATTCT | AATGCCTAGA | TTCTTTTGTG | GTTGTTGCTG | GCCCAATGAG | 1080 |
| TCCCTAGTCA | CATCCCCTGC | CAGAGGGAGT | TCTTCTTTTG | TGAGAGACAC | TGTAAACGAC | 1140 |
| ACAAGAGAAC | AAGAATAAAA | CAATAACTGT | G |  |  | 1171 |

( 2 ) INFORMATION FOR SEQ ID NO:4:

( i ) SEQUENCE CHARACTERISTICS:
        ( A ) LENGTH: 201 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Homo sapiens ( x i ) SEQUENCE DESCRIPTION: SEQ ID NO:4:

```
Met Thr Glu Lys Ala Pro Glu Pro His Val Glu Glu Asp Asp Asp
 1               5                  10                  15

Glu Leu Asp Ser Lys Leu Asn Tyr Lys Pro Pro Pro Gln Lys Ser Leu
            20                  25                  30

Lys Glu Leu Gln Glu Met Asp Lys Asp Asp Glu Ser Leu Ile Lys Tyr
        35                  40                  45

Lys Lys Thr Leu Leu Gly Asp Gly Pro Val Val Thr Asp Pro Lys Ala
    50                  55                  60

Pro Asn Val Val Val Thr Arg Leu Thr Leu Val Cys Glu Ser Ala Pro
65                  70                  75                  80

Gly Pro Ile Thr Met Asp Leu Thr Gly Asp Leu Glu Ala Leu Lys Lys
                    85                  90                  95

Glu Thr Ile Val Leu Lys Glu Gly Ser Glu Tyr Arg Val Lys Ile His
                100                 105                 110

Phe Lys Val Asn Arg Asp Ile Val Ser Gly Leu Lys Tyr Val Gln His
```

|     | 115 |     |     |     |     | 120 |     |     |     |     | 125 |     |     |     |
| --- | --- | --- | --- | --- | --- | --- | --- | --- | --- | --- | --- | --- | --- | --- |
| Thr | Tyr | Arg | Thr | Gly | Val | Lys | Val | Asp | Lys | Ala | Thr | Phe | Met | Val | Gly |
|     |     | 130 |     |     |     |     | 135 |     |     |     | 140 |     |     |     |     |
| Ser | Tyr | Gly | Pro | Arg | Pro | Glu | Glu | Tyr | Glu | Phe | Leu | Thr | Pro | Val | Glu |
| 145 |     |     |     |     | 150 |     |     |     |     | 155 |     |     |     | 160 |
| Glu | Ala | Pro | Lys | Gly | Met | Leu | Ala | Gln | Asp | Thr | Tyr | His | Asn | Lys | Ser |
|     |     |     |     | 165 |     |     |     |     | 170 |     |     |     |     | 175 |
| Phe | Phe | Thr | Asp | Asp | Lys | Gln | Asp | His | Leu | Ser | Trp | Glu | Trp | Asn |
|     |     |     | 180 |     |     |     | 185 |     |     |     |     | 190 |     |     |
| Leu | Ser | Ile | Lys | Lys | Glu | Trp | Thr | Glu |
|     |     | 195 |     |     |     |     | 200 |     |

( 2 ) INFORMATION FOR SEQ ID NO:5:

( i ) SEQUENCE CHARACTERISTICS:
        ( A ) LENGTH: 1107 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Murine ( x i ) SEQUENCE DESCRIPTION: SEQ ID NO:5:

| CGCCGACTGG | AGCCTGGAAT | AGAACAATCA | AGATGACGGA | GAAGGATGCA | CAGCCACAGC | 60 |
| --- | --- | --- | --- | --- | --- | --- |
| TGGAAGAGGC | GGACGACGAC | CTGGACAGCA | AGCTCAATTA | TAAGCCACCC | CCTCAGAAGT | 120 |
| CCTTGAAGGA | GCTGCAGGAG | ATGGACAAGG | ATGACGAGAG | TCTAACCAAG | TACAAGAAAA | 180 |
| CACTGCTGGG | AGATGTCCCT | GTGGTAGCAG | ACCCAACAGT | TCCCAATGTG | ACTGTTACCC | 240 |
| GGCTTAGCCT | TGTATGTGAC | AGTGCACCAG | GACCCATCAC | CATGGACCTT | ACTGGGGATC | 300 |
| TCGAGGCCCT | CAAAAAGGAT | ACATTTGTGC | TAAAGGAAGG | CATTGAATAC | AGGGTGAAAA | 360 |
| TTAACTTCAA | AGTGAATAAG | GATATTGTGT | CTGGCCTGAA | GTATGTTCAA | CACACATACC | 420 |
| GGACTGGCAT | GAGAGTGGAT | AAAGCCACAT | TCATGGTTGG | CAGCTATGGG | CCCCGACCAG | 480 |
| AGGAGTACGA | ATTCCTCACT | CCAGTAGAGG | AAGCTCCCAA | GGGCATGCTG | GCCCGAGGCA | 540 |
| CTTACCACAA | CAAGTCCTTC | TTCACGGATG | ACGACAAACA | GGACCACCTC | ACCTGGGAAT | 600 |
| GGAACCTGGC | CATTAAGAAG | GATTGGACAG | AATGAGTGCG | TCTGTCCGTC | CCTCCTGTCA | 660 |
| CCTTCCTCAC | CCACCAGAAG | AGTTCTCCCG | ACCATGTTGA | TCATCACAAA | CTCCCTCCTC | 720 |
| CCTCCCTGTT | CCTAGCTAGG | CCCTTTCTCT | GTCACACACA | CACACACACA | CATTTCATCA | 780 |
| CCAATATGTT | TTATCTTACC | CCATCTCTCA | GAGTGTTCCC | TGCAAATGAG | ACTTAAAACC | 840 |
| CTGGCTTCTC | CCACCTTGAG | TCCTGAAGGT | CAAGAAATGG | GCAAGCTCCG | GCTGACGCCT | 900 |
| CCTTGGCCTT | CTGTTCAGAA | GTTTATTCTT | GCCACTGGGT | TCTTCCGGTT | CGATGAACCC | 960 |
| CGTTGTCTTC | TCTGCCAAGG | GGAGCTCTCC | TTTTGTGGGA | GACACTGTAA | ACAACACCAA | 1020 |
| AGGAAAAGAA | TAAAATCGTT | GTGTGTGTGA | CTGAGAACCT | CATTTGCTTT | CCTTTGCCCT | 1080 |
| TAAATAAATA | TGGTACCAGA | AAAAAA |     |     |     | 1107 |

( 2 ) INFORMATION FOR SEQ ID NO:6:

( i ) SEQUENCE CHARACTERISTICS:
        ( A ) LENGTH: 201 amino acids (B) TYPE: amino acid
(C) STRANDEDNESS: single
(D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
(A) ORGANISM: Murine (xi) SEQUENCE DESCRIPTION: SEQ ID NO:6:

| Met | Thr | Glu | Lys | Asp | Ala | Gln | Pro | Gln | Leu | Glu | Glu | Ala | Asp | Asp |
|---|---|---|---|---|---|---|---|---|---|---|---|---|---|---|
| 1 | | | | 5 | | | | | 10 | | | | | 15 |

| Leu | Asp | Ser | Lys | Leu | Asn | Tyr | Lys | Pro | Pro | Pro | Gln | Lys | Ser | Leu | Lys |
|---|---|---|---|---|---|---|---|---|---|---|---|---|---|---|---|
| | | | 20 | | | | 25 | | | | | | 30 | | |

| Glu | Leu | Gln | Glu | Met | Asp | Lys | Asp | Asp | Glu | Ser | Leu | Thr | Lys | Tyr | Lys |
|---|---|---|---|---|---|---|---|---|---|---|---|---|---|---|---|
| | | 35 | | | | | 40 | | | | | 45 | | | |

| Lys | Thr | Leu | Leu | Gly | Asp | Val | Pro | Val | Val | Ala | Asp | Pro | Thr | Val | Pro |
|---|---|---|---|---|---|---|---|---|---|---|---|---|---|---|---|
| | 50 | | | | | 55 | | | | | 60 | | | | |

| Asn | Val | Thr | Val | Thr | Arg | Leu | Ser | Leu | Val | Cys | Asp | Ser | Ala | Pro | Gly |
|---|---|---|---|---|---|---|---|---|---|---|---|---|---|---|---|
| 65 | | | | | 70 | | | | | 75 | | | | | 80 |

| Pro | Ile | Thr | Met | Asp | Leu | Thr | Gly | Asp | Leu | Glu | Ala | Leu | Lys | Lys | Asp |
|---|---|---|---|---|---|---|---|---|---|---|---|---|---|---|---|
| | | | | 85 | | | | | 90 | | | | | 95 | |

| Thr | Phe | Val | Leu | Lys | Glu | Gly | Ile | Glu | Tyr | Arg | Val | Lys | Ile | Asn | Phe |
|---|---|---|---|---|---|---|---|---|---|---|---|---|---|---|---|
| | | | 100 | | | | | 105 | | | | | 110 | | |

| Lys | Val | Asn | Lys | Asp | Ile | Val | Ser | Gly | Leu | Lys | Tyr | Val | Gln | His | Thr |
|---|---|---|---|---|---|---|---|---|---|---|---|---|---|---|---|
| | | 115 | | | | | 120 | | | | | 125 | | | |

| Tyr | Arg | Thr | Gly | Met | Arg | Val | Asp | Lys | Ala | Thr | Phe | Met | Val | Gly | Ser |
|---|---|---|---|---|---|---|---|---|---|---|---|---|---|---|---|
| | 130 | | | | | 135 | | | | | 140 | | | | |

| Tyr | Gly | Pro | Arg | Pro | Glu | Glu | Tyr | Glu | Phe | Leu | Thr | Pro | Val | Glu | Glu |
|---|---|---|---|---|---|---|---|---|---|---|---|---|---|---|---|
| 145 | | | | | 150 | | | | | 155 | | | | | 160 |

| Ala | Pro | Lys | Gly | Met | Leu | Ala | Arg | Gly | Thr | Tyr | His | Asn | Lys | Ser | Phe |
|---|---|---|---|---|---|---|---|---|---|---|---|---|---|---|---|
| | | | | 165 | | | | | 170 | | | | | 175 | |

| Phe | Thr | Asp | Asp | Asp | Lys | Gln | Asp | His | Leu | Thr | Trp | Glu | Trp | Asn | Leu |
|---|---|---|---|---|---|---|---|---|---|---|---|---|---|---|---|
| | | | 180 | | | | | 185 | | | | | 190 | | |

| Ala | Ile | Lys | Lys | Asp | Trp | Thr | Glu | Glx |
|---|---|---|---|---|---|---|---|---|
| | | 195 | | | | | 200 | |

(2) INFORMATION FOR SEQ ID NO:7:

(i) SEQUENCE CHARACTERISTICS:
(A) LENGTH: 96 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (v) ORIGINAL SOURCE:
(A) ORGANISM: Synthetic (xi) SEQUENCE DESCRIPTION: SEQ ID NO:7:

```
TCGAGCTCGG TACCCGGCCG GGGATCCATC GAGGGTAGGC CTGAATTCAG TAAAACCCTC    60
GATGGATCCT CTAGAGTCGA CCTGCAGGCA AGCTTG                              96
```

( 2 ) INFORMATION FOR SEQ ID NO:8:

( i ) SEQUENCE CHARACTERISTICS:
        ( A ) LENGTH: 204 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Bovine
        ( F ) TISSUE TYPE: Brain ( x i ) SEQUENCE DESCRIPTION: SEQ ID NO:8:

```
Met Ala Glu Gln Glu Pro Thr Ala Glu Gln Leu Ala Gln Ile Ala Ala
 1               5                  10                  15

Glu Asn Glu Glu Asp Glu His Ser Val Asn Tyr Lys Pro Pro Ala Gln
            20                  25                  30

Lys Ser Ile Gln Glu Ile Gln Glu Leu Asp Lys Asp Asp Glu Ser Leu
        35                  40                  45

Arg Lys Tyr Lys Glu Ala Leu Leu Gly Arg Val Ala Val Ser Ala Asp
    50                  55                  60

Pro Asn Val Pro Asn Val Val Thr Arg Leu Thr Leu Val Cys Ser
65                  70                  75                  80

Thr Ala Pro Gly Pro Leu Glu Leu Asp Leu Thr Gly Asp Leu Glu Ser
                85                  90                  95

Phe Lys Lys Gln Ser Phe Val Leu Lys Glu Gly Val Glu Tyr Arg Ile
               100                 105                 110

Lys Ile Ser Phe Arg Val Asn Arg Glu Ile Val Ser Gly Met Lys Tyr
           115                 120                 125

Ile Gln His Thr Tyr Arg Lys Gly Val Lys Ile Asp Lys Thr Asp Tyr
       130                 135                 140

Met Val Gly Ser Tyr Gly Pro Arg Ala Glu Glu Tyr Glu Phe Leu Thr
145                 150                 155                 160

Pro Met Glu Glu Ala Pro Lys Gly Met Leu Ala Arg Gly Ser Tyr Asn
               165                 170                 175

Ile Lys Ser Arg Phe Thr Asp Asp Asp Arg Thr Asp His Leu Ser Trp
           180                 185                 190

Glu Trp Asn Leu Thr Ile Lys Lys Glu Trp Lys Asp
           195                 200
```